(12) United States Patent
Jones et al.

(10) Patent No.: US 10,451,784 B2
(45) Date of Patent: Oct. 22, 2019

(54) TEMPERATURE INVARIANT INFRARED FILTER

(71) Applicants: SCHLUMBERGER TECHNOLOGY CORPORATION, Sugar Land, TX (US); READING UNIVERSITY, Reading Berkshire (GB)

(72) Inventors: Timothy Jones, Cambridge (GB); Nathan Lawrence, Cambridge (GB); Gary Hawkins, Reading (GB); Richard Sherwood, Reading (GB); Karim Djotni, Reading (GB)

(73) Assignees: SCHLUMBERGER TECHNOLOGY CORPORATION, Sugar Land, TX (US); UNIVERSITY OF READING, Reading (GB)

( * ) Notice: Subject to any disclaimer, the term of this patent is extended or adjusted under 35 U.S.C. 154(b) by 0 days.

(21) Appl. No.: 15/511,491

(22) PCT Filed: Sep. 9, 2015

(86) PCT No.: PCT/US2015/049094
§ 371 (c)(1),
(2) Date: Mar. 15, 2017

(87) PCT Pub. No.: WO2016/048655
PCT Pub. Date: Mar. 31, 2016

(65) Prior Publication Data
US 2018/0321428 A1    Nov. 8, 2018

(30) Foreign Application Priority Data

Sep. 15, 2014 (GB) .................................... 1416268.9

(51) Int. Cl.
*G02B 5/28* (2006.01)
*G01N 33/28* (2006.01)
*G01J 3/02* (2006.01)

(52) U.S. Cl.
CPC ................ *G02B 5/285* (2013.01); *G01J 3/02* (2013.01); *G01N 33/2823* (2013.01); *G02B 5/281* (2013.01)

(58) Field of Classification Search
None
See application file for complete search history.

(56) References Cited

U.S. PATENT DOCUMENTS

| 4,922,714 A | 5/1990 | Grob et al. |
| 5,049,742 A | 9/1991 | Hosonuma et al. |

(Continued)

FOREIGN PATENT DOCUMENTS

| CN | 101893558 A | 11/2010 |
| DE | 10255769 A1 | 6/2004 |

(Continued)

OTHER PUBLICATIONS

Hawkins, G. et al., "Cooled infrared filters and dichroics for the sea and land surface temperature radiometer", Applied Optics, 2013, 52(10), pp. 2125-2135.

(Continued)

*Primary Examiner* — Darryl J Collins
*Assistant Examiner* — Journey F Sumlar

(57) ABSTRACT

A narrow bandpass filter that may be used in a mid-infrared sensor for monitoring a species, which may be a component of a fluid or a solid material. The filter comprises a cavity comprising a low refractive index material. By providing a high ratio of low refractive index material in the filter with respective to high refractive index material, the filter is configured so that wavelength transmission remains con- (Continued)

stant with varying temperature. Materials used for the low and/or high refractive index provide a temperature invariant filter that transmits mid-infrared spectra without serious degradation.

20 Claims, 20 Drawing Sheets

(56) References Cited

U.S. PATENT DOCUMENTS

| | | | |
|---|---|---|---|
| 5,859,430 | A | 1/1999 | Mullins et al. |
| 6,147,762 | A | 11/2000 | Haschberger et al. |
| 6,215,592 | B1 | 4/2001 | Pelekhaty |
| 6,343,167 | B1 | 1/2002 | Scalora et al. |
| 6,507,396 | B1 | 1/2003 | Godfried et al. |
| 6,627,873 | B2 | 9/2003 | Tchakarov et al. |
| 6,958,818 | B1 * | 10/2005 | Payne ................ G01J 3/26 356/519 |
| 6,995,360 | B2 | 2/2006 | Jones et al. |
| 7,123,416 | B1 | 10/2006 | Erdogan et al. |
| 7,407,566 | B2 | 8/2008 | Jiang et al. |
| 7,697,141 | B2 | 4/2010 | Jones et al. |
| 7,804,598 | B2 | 9/2010 | Hall et al. |
| 9,013,702 | B2 | 4/2015 | Freese |
| 2003/0062472 | A1 | 4/2003 | Mullins et al. |
| 2003/0147159 | A1 | 8/2003 | Dube et al. |
| 2005/0269499 | A1 | 12/2005 | Jones et al. |
| 2006/0097203 | A1 | 5/2006 | Bykanov et al. |
| 2006/0139646 | A1 | 6/2006 | DiFoggio |
| 2006/0175547 | A1 | 8/2006 | DiFoggio et al. |
| 2006/0177939 | A1 | 8/2006 | Lehmann et al. |
| 2008/0165356 | A1 | 7/2008 | Difoggio et al. |
| 2008/0173805 | A1 | 7/2008 | Indo et al. |
| 2010/0195105 | A1 | 8/2010 | Myrick et al. |
| 2011/0228279 | A1 * | 9/2011 | Lucey ................ G01J 3/26 356/454 |
| 2012/0025103 | A1 | 2/2012 | Deshmukh et al. |
| 2012/0170023 | A1 | 7/2012 | Szobota et al. |
| 2012/0290208 | A1 | 11/2012 | Jiang et al. |
| 2013/0056626 | A1 | 3/2013 | Shen et al. |
| 2013/0070231 | A1 | 3/2013 | Nauka et al. |
| 2013/0284900 | A1 | 10/2013 | Freese et al. |
| 2014/0076551 | A1 | 3/2014 | Pelletier et al. |
| 2017/0241899 | A1 | 8/2017 | Jones et al. |
| 2017/0242149 | A1 | 8/2017 | Fujisawa et al. |
| 2017/0242150 | A1 | 8/2017 | Jones et al. |
| 2018/0231684 | A1 | 8/2018 | Jones et al. |

FOREIGN PATENT DOCUMENTS

| | | |
|---|---|---|
| DE | 102010045643 A1 | 3/2012 |
| EP | 0795744 A1 | 9/1997 |
| EP | 1967872 A1 | 9/2008 |
| GB | 2345753 A | 7/2000 |
| GB | 2395553 A | 5/2004 |
| GB | 2402476 A | 12/2004 |
| GB | 2507959 A | 5/2014 |
| JP | S5831307 A | 2/1983 |
| JP | 2013054368 A | 3/2013 |
| KR | 20120075182 A | 7/2012 |
| WO | WO0140771 A2 | 6/2001 |
| WO | WO2006063094 A1 | 6/2006 |
| WO | WO2009000490 A1 | 12/2008 |
| WO | WO2012073791 A1 | 6/2012 |
| WO | WO2016044008 A1 | 3/2016 |

OTHER PUBLICATIONS

Baker, M. L. et al., "Effects of the Variation of Angle of Incidence and Temperature on Infrared Filter Characteristics", Applied Optics, 1967, 6(8), pp. 1343-1351.

Belyaeva, A. I., "Cryogenic infrared multilayer filters: the origin of low temperature shift in the pass-band edge", Proceedings of SPIE, 1999, 3890, pp. 87-92.

Blifford, I. H., "Factors Affecting the Performance of Commercial Interference Filters", Applied Optics, 1966, 5(1), pp. 105-111.

Born, M. et al., "Principles of Optics", pp. 323-333, 6th edition, Pergamon Press, Oxford (1980).

Chen, T-C. et al., "Influences of Temperature and Stress on Transmission Characteristics of Multilayer Thin-Film Narrow Bandpass Filters", Japanese Journal of Applied Physics, Part 1, 40(6A), pp. 4087-4096.

Evans, C. S. et al., "Filters for v2 band of CO2: monitoring and control of layer deposition", Applied Optics, 1976, 15 (11), pp. 2736-2745.

Harrick, N. J., "Internal Reflection Spectroscopy", Wiley Interscience, New York, New York, USA, 1967, pp. 43-44.

Heath, D. F., et al., "Characterization of a "hardened" ultrastable UV linear variable filter and recent results on the radiometric stability of narrow band interference filters subjected to temperature/humidity, thermal/vacuum and ionizing radiation environments", SPIE, 1998, 3501, pp. 401-411.

Kaplan, S. G. et al., "Characterization of narrowband infrared interference filters", Proceeding of SPIE, 1998, 3425, 48-55.

Kim, S-H. et al., "Temperature Dependence of Transmission Center Wavelength of Narrow Bandpass Filters Prepared by Plasma Ion-Assisted Deposition", Journal of Korean Physical Society, 2004, 45(1), pp. 93-98.

Li, B.et al., "Improving low-temperature performance of infrared thin-film interference filters utilizing the intrinsic properties of IV-VI narrow-gap semiconductors", Optics Express, 2004, 12(3),pp. 401-404.

Li, B. et al., "Recent progress in improving low-temperature stability of infrared thin-film interference filters", Optics Express, 2005, 13(17), pp. 6376-6380.

Macleod, H. A., "Thin-Film Optical Filters", 4th edition, pp. 489-568, CRC Press, Boca Raton, Florida (2010).

Mansuno, K. et al., "Enhanced Contrast of Wavelength-Selective Mid-Infrared Detectors Stable Against Incident Angle and Temperature Changes", Japanese Journal of Applied Physics, 2011, 50(3R), pp. 037201 (7 pages).

Piccioli, N. et al., "Optical Constants and Band Gap of PbTe from Thin Film Studies Between 25 and 300 K", Journal of Physics Chemical Solids, 1974, 35, pp. 971-977.

Ritter, E. et al., "Influence of Substrate Temperature on the Condensation of Vacuum Evaporated Films of MgF2 and ZnS", Journal of Vacuum Science and Technology, 1969, 6, pp. 733-736.

Sakaguchi, S., "Temperature Dependence of Transmission Characteristics of Multilayer Film Narrow Bandpass Filters", Japanese Journal of Applied Physics, 1999, 38, pp. 6362-6368.

Seeley, J. S. et al., "Temperature-invariant and other narrow-band IR filters containing PbTe, 4-20 [micrometers]", Proceedings of the Society of Photo-Optical Instrumentation Engineers, 1980, 246, pp. 83-94.

Takahashi, H., "Temperature stability of thin-film narrow-bandpass filters produced by ion-assisted deposition", Applied Optics, 1995, 34(4), pp. 667-675.

Thelen, A., "Multilayer Filters with Wide Transmittance Bands", Journal of the Optical Society of America, 1963, 53 (11), pp. 1266-1279.

Tsai, R-Y., et al., "Thermally stable narrow-bandpass filter prepared by reactive ion-assisted sputtering", Applied Optics, 2001, 40(10), pp. 1593-1598.

Weiting, F. et al., "Temperature Effects on the Refractive Index of Lead Telluride and Zinc Selenide", Infrared Physics, 1990, 30(4), pp. 371-373.

Wiechmann, S. et al., "Thermo-optic properties of TiO2, Ta2O5 and Al2O3 thin films for integrated optics on silicon", Thin Solid Films, 2009 517(24), pp. 6847-6849.

Zemel, J. N. et al., "Electrical and Optical Properties of Epitaxial Films of PbS PbSe PbTe and SnTe", Shys. Rev, 1965, 140, pp. A330-A343.

Roithner LaserTechnik GmbH Mid-IR Products Brochure, Sep. 2010, 4 pages.

(56) References Cited

OTHER PUBLICATIONS

Combined Search and Exam Report under Sections 17 and 18(3) in corresponding United Kingdom patent application No. 1416268.9 dated Jan. 29, 2015, 9 pages.
Combined Search and Exam Report under Sections 17 and 18(3) in corresponding United Kingdom patent application No. 1416256.4 dated Mar. 16, 2015, 6 pages.
Search Report and Written Opinion of International Patent Application No. PCT/US2015/049058 dated Dec. 23, 2015, 15 pages.
Combined Search and Exam Report under Sections 17 and 18(3) in corresponding United Kingdom patent application No. 1416257.2 dated Jan. 14, 2015, 6 pages.
Search Report and Written Opinion of International Patent Application No. PCT/US2015/049065, dated Nov. 24, 2015, 18 pages.
Combined Search and Exam Report under Sections 17 and 18(3) in corresponding United Kingdom patent application No. 1416260.6 dated Jan. 26, 2015, 5 pages.
Search Report and Written Opinion of International Patent Application No. PCT/US2015/049554, dated Dec. 23, 2015, 8 pages.
Office Action issued in related U.S. Appl. No. 15/511,343 dated Feb. 21, 2018, 26 pages.
Combined Search and Exam Report under Sections 17 and 18(3) in corresponding United Kingdom patent application No. 1416264.8 dated Mar. 16, 2015, 6 pages.
Search Report and Written Opinion of International Patent Application No. PCT/US2015/049086 dated Dec. 21, 2015, 15 pages.
Office Action issued in related U.S. Appl. No. 15/511,336 dated Jun. 18, 2018, 14 pages.
Combined Search and Exam Report under Sections 17 and 18(3) in corresponding United Kingdom patent application No. 1416265.5 dated Mar. 12, 2015, 8 pages.
Exam Report under Section 18(3) in corresponding United Kingdom patent application No. 1416265.5 dated Oct. 4, 2016, 3 pages.
Search Report and Written Opinion of International Patent Application No. PCT/US2015/049061 dated Dec. 23, 2015, 17 pages.
Exam Report under Section 18(3) in corresponding United Kingdom patent application No. 1416268.9 dated Aug. 29, 2017, 5 pages.
CSI Technologies: Analytical Testing and Analysis C54:D57//csi-tech.net/assets/literature/analytical-testing-and-analysis.pdf (CSI Industries) (2 pages).
Tropf et al: Optical materials: visible and infrared, Chapter 11 of Electro-Optics Handbook (R.W. Waynant and M.N. Ediger, eds.), Second edition, McGraw-Hill, New York (2000) 125 pages.

* cited by examiner

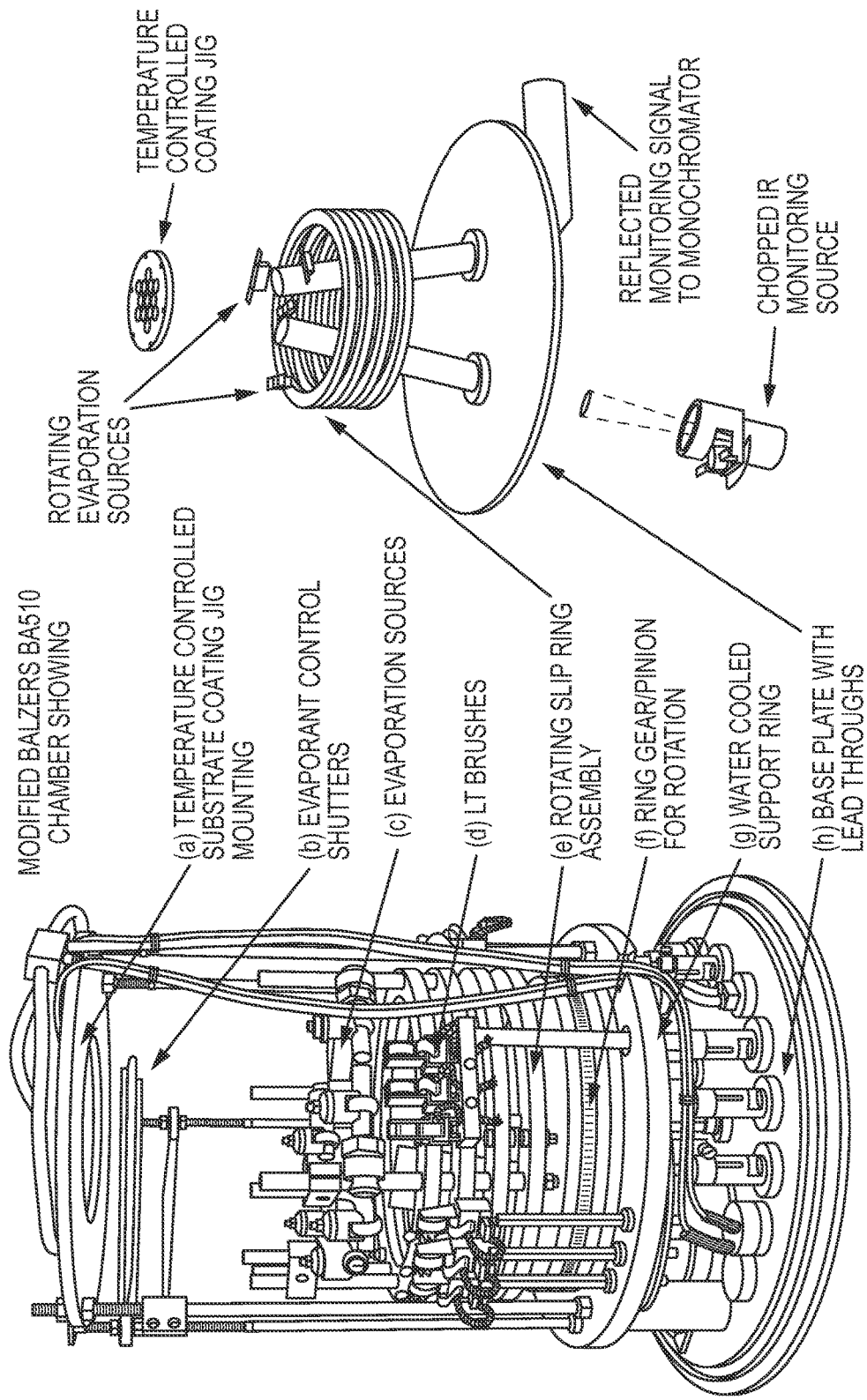

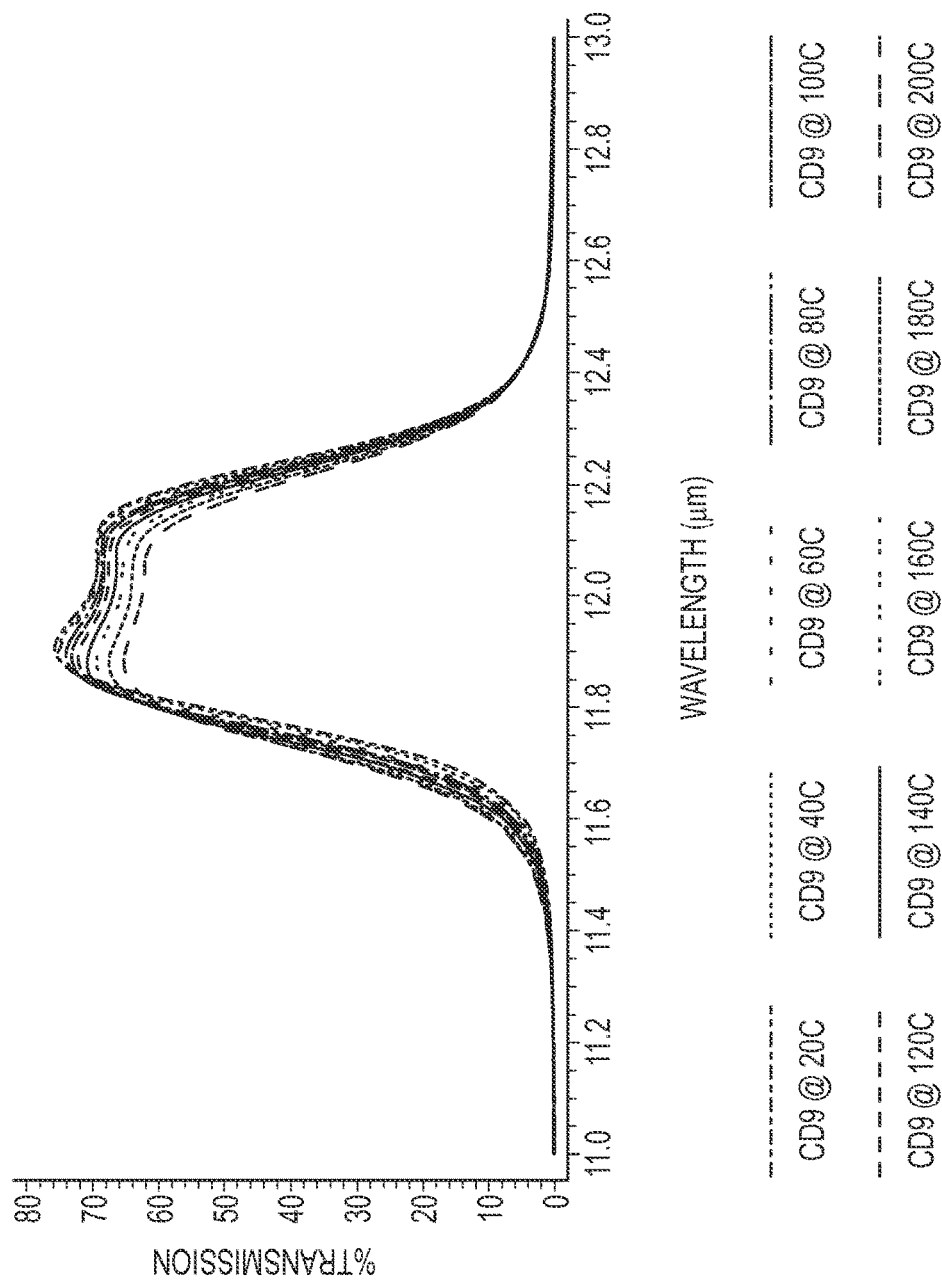

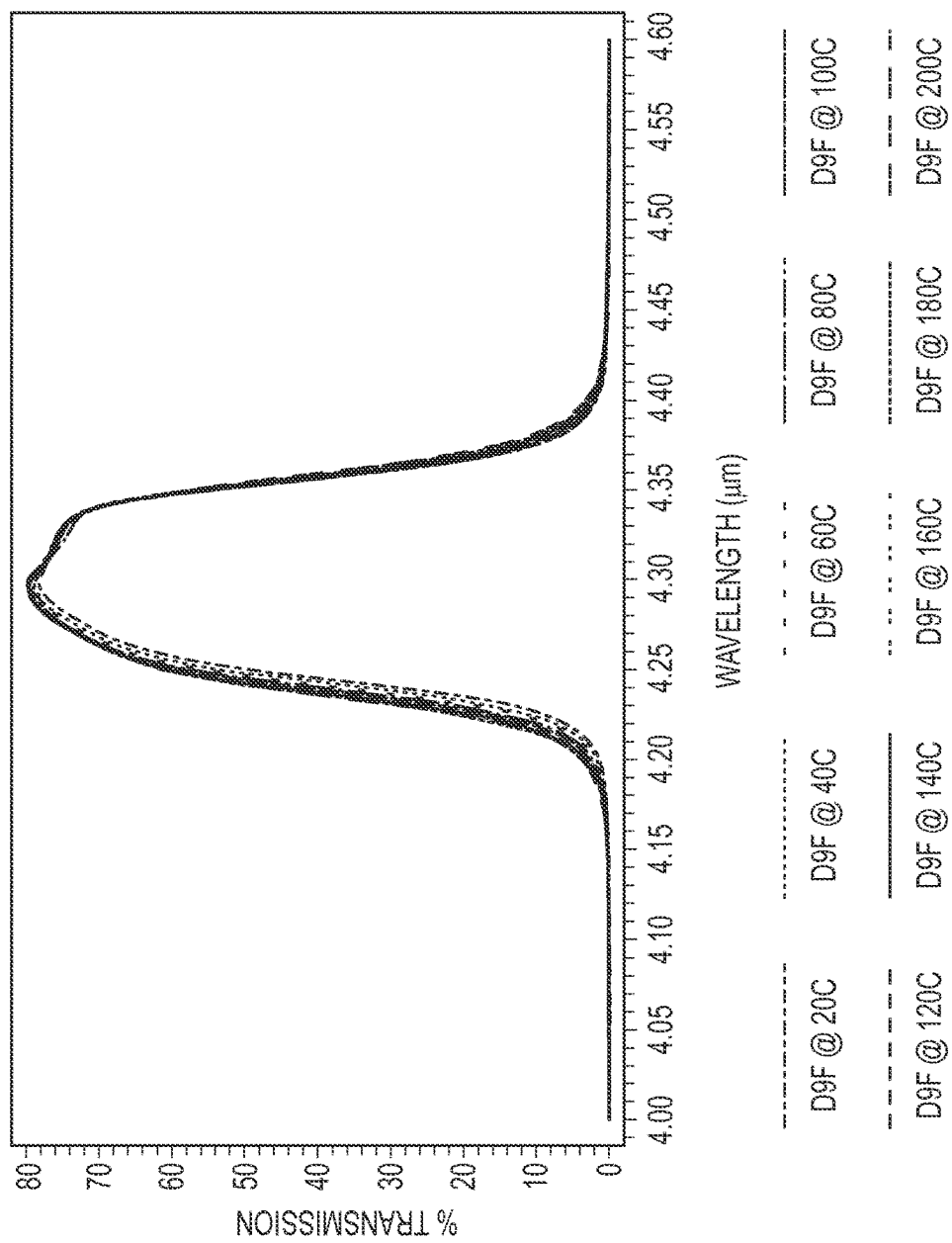

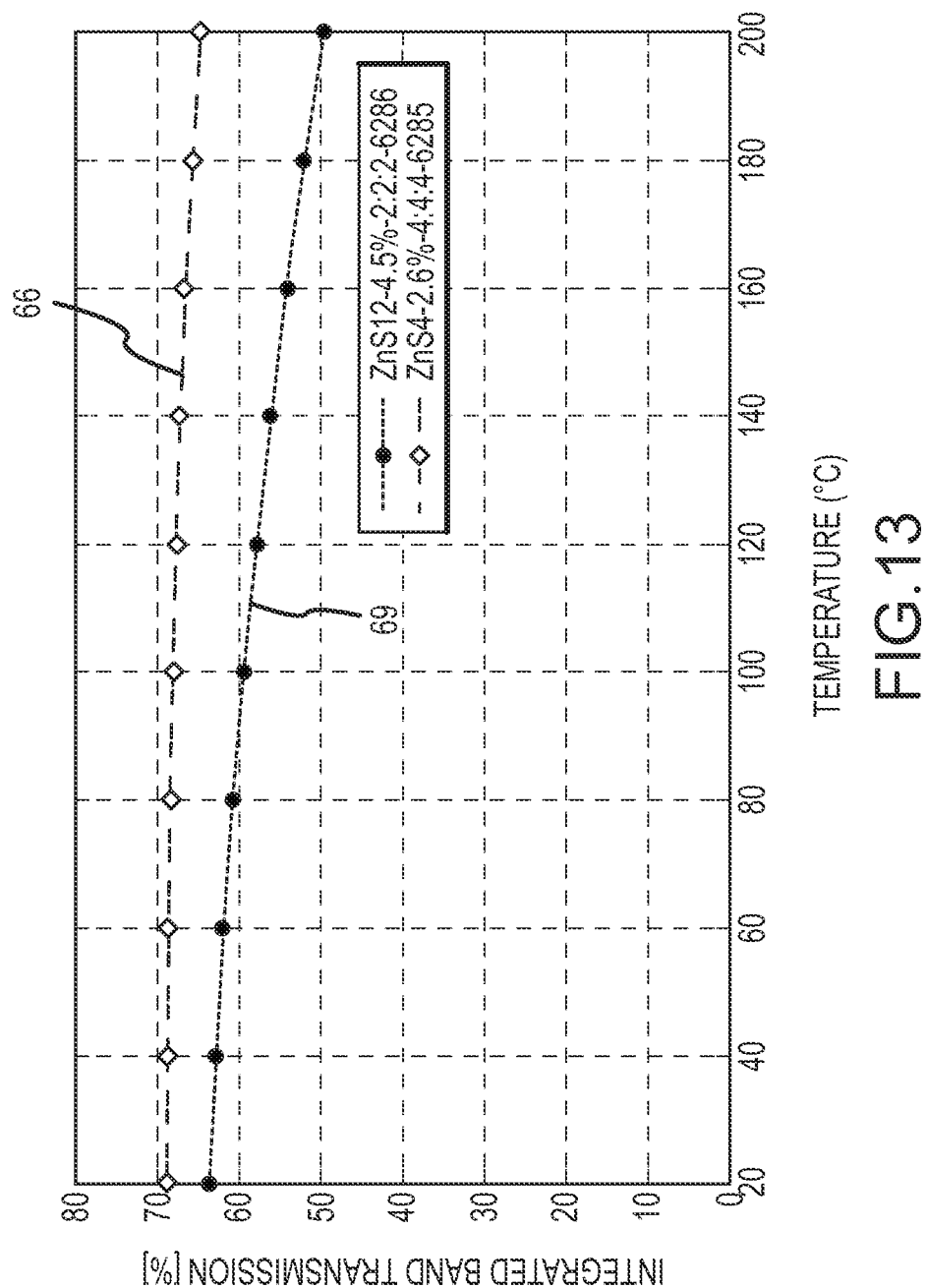

TEMPERATURE INVARIANT INFRARED FILTER

BACKGROUND

Embodiments of the present disclosure relate to narrow bandpass filter that may be used in a mid-infrared sensor for monitoring a species, which may be a component of a fluid or a solid material.

The analysis of chemical composition of fluid samples is important in many industries and is often required to be performed in harsh environments. For example, in the food and beverage and chemical processing industries, online measurements are often required to be made in hot, cold, widely temperature varying conditions and/or in the presence of reactive compounds. In the hydrocarbon industry, online measurements are often made in hydrocarbon wells for the determination of phase behaviour and chemical composition for the monitoring and management of a hydrocarbon well as well as the evaluation of the producibility and economic value of the hydrocarbon reserves. Similarly, the monitoring of fluid composition during production or other operations can have an important bearing on reservoir management decisions. Similarly, determination of phase behaviour and chemical composition is important in pipelines and the like used to convey/transport hydrocarbons from the wellhead, including subsea pipelines.

SUMMARY

Embodiments of the present disclosure provide mid-infrared sensors for use where temperatures may vary widely.

For purposes of the present disclosure, the term "mid-infrared radiation" means that the radiation has a wavelength in the range from about 2 to 25 μm, and in some embodiments of the disclosure from about 3 to 12 μm or from about 3 to 10 μm.

In embodiments of the present disclosure, a narrow bandpass filter may be configured such that its wavelength transmission band is substantially temperature invariant over all temperatures in the range from about 25 to 150° C. In some embodiments, the narrow bandpass filter may be configured for use in the petrochemical industry, where temperatures in downhole environments can vary greatly, e.g. from room temperature up to 150° C. or 200° C. By using such a temperature invariant filter, the sensitivity of the sensor to shifts in temperature of its surroundings can be greatly reduced, improving accuracy and allowing for use of mid-infrared sensing techniques in locations experiencing wide temperature fluctuations.

To cover a greater range of downhole temperatures, the wavelength transmission band of the first narrow bandpass filter may be substantially temperature invariant over all temperatures in the range from about 25 to 200° C. To cover both downhole and subsea conditions (where ambient temperatures can be in the range from −25 to 25° C.), the wavelength transmission band of the first narrow bandpass filter may be substantially temperature invariant over all temperatures in the range from about −25 to 125, 150 or 200° C.

In embodiments of the present disclosure, the term "substantially temperature invariant" means that the variance is at most about 0.2 nm/° C over the temperature range −25 to +200° C. and over the wavelength range 2-14 μm. In some embodiments, the variance is at most about 0.05, 0.03, 0.02 or 0.01 nm/° C.

In some embodiments of the present disclosure, the filter may be an interference filter. For example, the filter may in some embodiments comprise a substrate, formed of Si, $SiO_2$, $Al_2O_3$, Ge, ZnSe and/or the like and at each opposing side of the substrate alternating high and low refractive index layers may be formed. For example, in some embodiments, the high refractive index layers may be formed of PbTe, PbSe, PbS and/or the like and the low refractive index layers may be formed of ZnS, ZnSe and/or the like.

Applicants have found that for mid-infrared filters experiencing wide temperature variations, changes in optical properties of the filter may be prevented by controlling the ratio of low to high refractive index materials in the filter so that there is a high ratio of the low refractive index material. To produce this, in some embodiments of the present disclosure, the cavities of the low bandpass filter comprise low refractive index material. In embodiments of the present disclosure, filter comprises a cavity having an optical thickness of at least three full wavelengths of the transmission wavelength or the narrow band of transmission wavelengths or three half-wavelengths of the transmission wavelength or the narrow band of transmission wavelengths. In some embodiments, the filter comprises at least separate three cavities. For example, where the filter comprises at least three separate cavities, each of the cavities are either half wavelength ($\lambda/2$) or full wavelength ($\lambda$) of the transmitted radiation in optical thickness. And for example, where the cavity comprises a single cavity, it comprises a cavity of optical thickness $3\lambda/2$ or $3\lambda$, in optical thickness. In some embodiments, other combinations of cavities are used to obtain a narrow bandpass filter comprising a cavity with an optical thickness of three full wavelengths of the transmission wavelength or the narrow band of transmission wavelengths or three half-wavelengths of the transmission wavelength or the narrow band of transmission wavelengths, e.g., one cavity with a half wavelength ($\lambda/2$) optical thickness and one cavity with a full wavelength ($\lambda$) optical thickness.

Many conventional filters display changes in optical properties, such as high band shifts, with increasing temperature. For example, shifts in the range 0.2 to 0.6 nm/° C. have typically been measured over narrow temperature ranges and/or at single wavelengths. Transmissivities of conventional filters also tend to reduce with increasing temperature. However, in embodiments of the present disclosure, by using a PbTe-based, PbSe-based, PbS-based and/or the like interference filter, it is possible to substantially reduce band shifts and transmissivity reductions. For example, a PbTe-based interference filter can, in accordance with an embodiment of the present disclosure, have a band shift of only about 0.03 nm/° C. or less. As an alternative to PbTe, PbSe, PbS or mixtures of these lead chalcogenide compounds may be used in some embodiments, for the high refractive index layers of the temperature invariant filter. Moreover, applicants have found that other high refractive index materials, such as germanium, are unsuitable for such filters.

BRIEF DESCRIPTION OF THE DRAWINGS

Embodiments of the disclosure will now be described by way of example with reference to the accompanying drawings in which:

FIG. 6A is an illustration of a Balzers BA510 thin film deposition system and FIG. 6B is a schematic of the rotating evaporation sources;

FIGS. 8A and 8B show the corresponding performance of two narrow bandpass filters, a degenerate filter in FIG. 8A and an optimally matched filter in FIG. 8B, operating at $\lambda_m$=12.12 μm;

FIGS. 11A and 11B show the temperature dependence of the bandpass of two 3 cavity filters fabricated on ZnS substrates that have been designed to operate at $\lambda_m$=4.26 μm (4:4:4 cavity layers) and $\lambda_m$=12.1 μm (2:2:2 cavity layers);

FIG. 13 shows the variation of Ti with temperature for the two filters of FIGS. 11A and 11B deposited on ZnS substrates.

Figure 1:
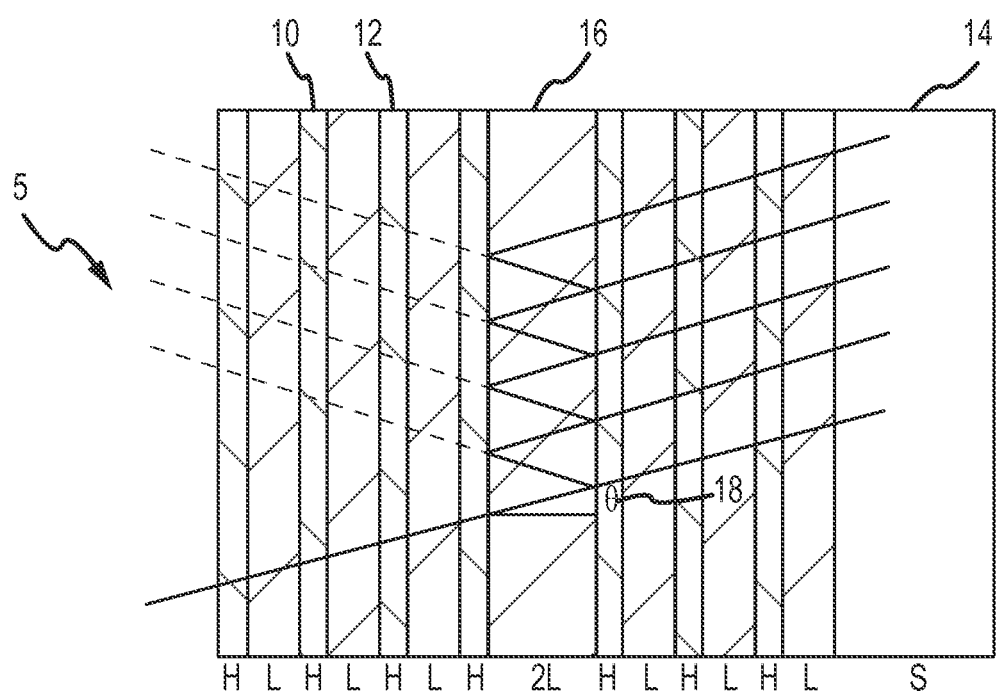
FIG. 1 shows a schematic of a typical structure of a narrow bandpass interference filter.
Figure 2A:
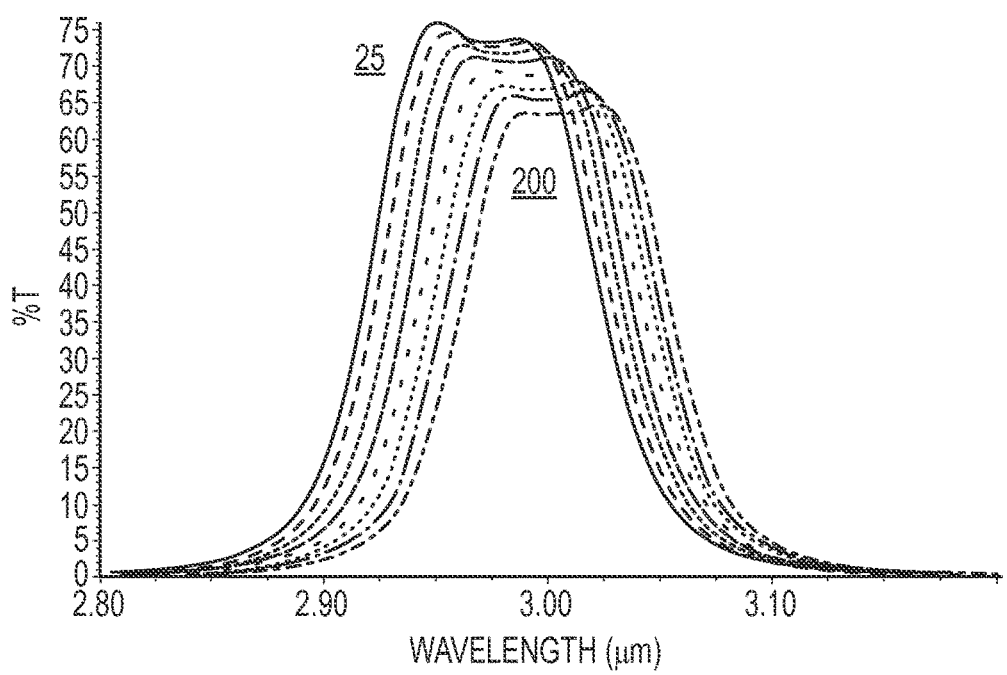
FIGS. 2A-2D illustrate temperature dependence of the bandpass of commercially-available filters A, B, C and D for the temperature range 25° C. to 200° C. in increments of 25° C.
Figure 2B:
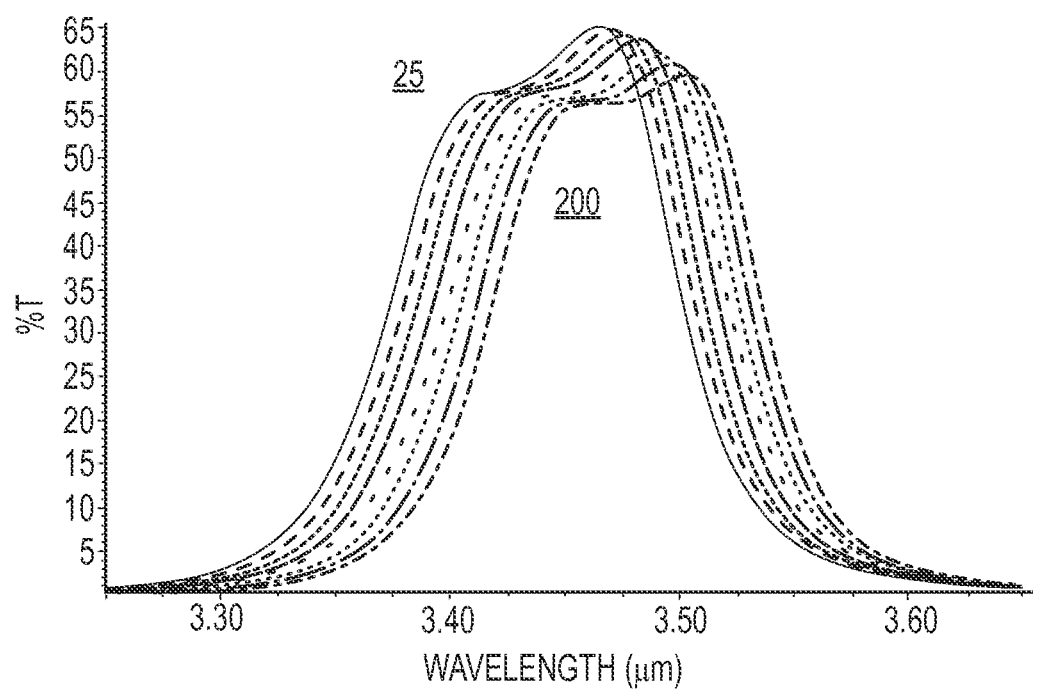
Figure 2C:
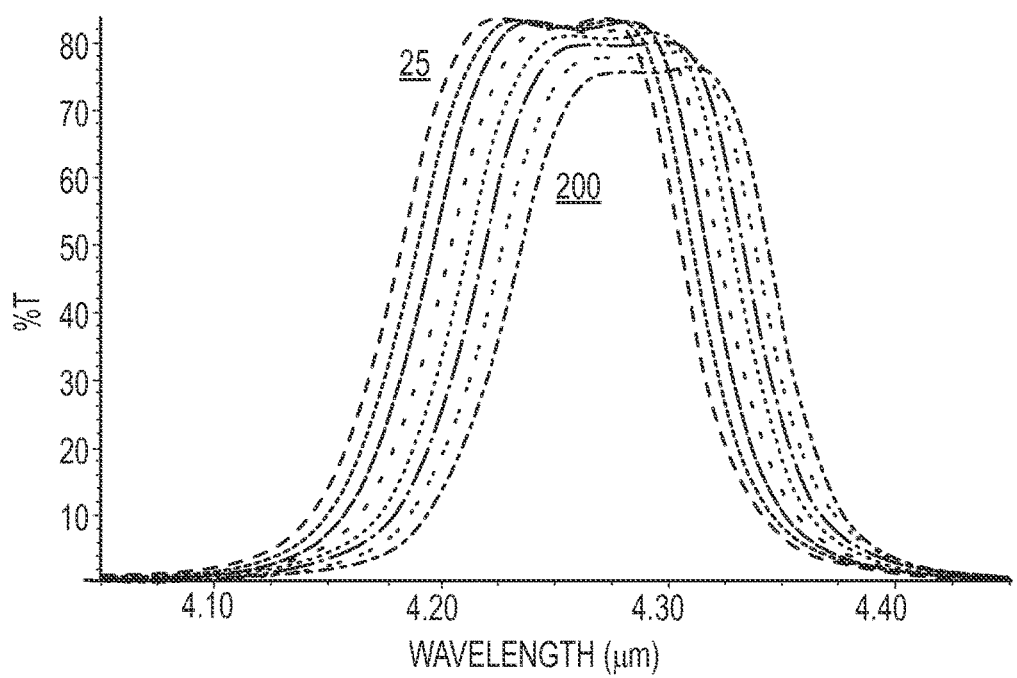
Figure 2D:
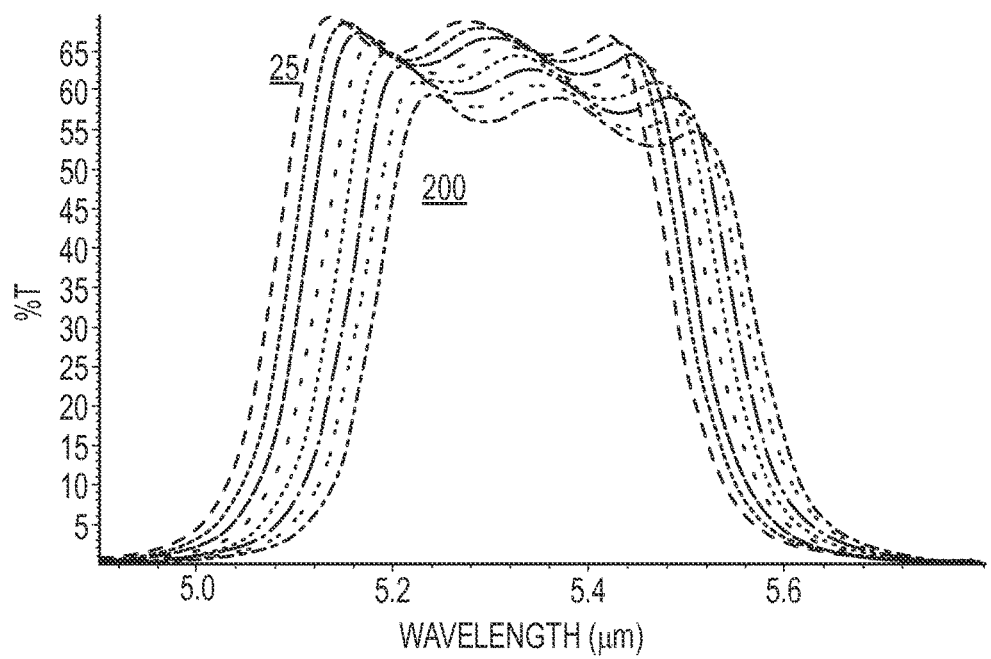

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention, it being understood that various changes may be made in the function and arrangement of elements without departing from the scope of the invention.

Specific details are given in the following description to provide a thorough understanding of the embodiments. However, it will be understood by one of ordinary skill in the art that embodiments may be practised without these specific details. For example, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

The spectral region of narrow bandpass dielectric filters designed to operate in the near-infrared ("near-IR") and mid-infrared ("mid-IR") shift systematically to longer wavelengths with increasing temperature. For example, tests have been performed to measure values of the shift in the wavelength ($\lambda_m$) at peak transmission with temperature, expressed as the temperature coefficient ($d\lambda_m/dT$), of a suite of commercially-available narrow bandpass filters operating in the near-IR spectral region ($\lambda_m$=0.39-1.02 µm). Values of $d\lambda_m/dT$ have been measured in the range of 0.001-0.003 nm/K with $\lambda_m$=0.32-1.02 µm, and 0.0025 nm/K over the temperature range 25-60° C. and 0.0036 nm/K over the temperature range 60-100° C. with $\lambda_m$=1.54 µm.

Significantly larger values of $d\lambda_m/dT$ have been measured for narrow bandpass filters operating in the mid-IR spectral region. For example, for a filter with $\lambda_m$=2.67 µm heated between 20° C. to 150° C. produced a value of $d\lambda_m/dT$ of 0.19 nm/K, while for a filter with $\lambda_m$=3.84 µm cooled from 20° C. cooling to −190° C. produced a corresponding value of 0.33 nm/K. Moreover, the width of the bandpass regions for mid-IR filters have been found to decrease on heating. Values of $d\lambda_m/dT$ reported in the literature for mid-IR filters are in the range 0.2-0.8 nm/K.

The origin of the change in $\lambda_m$ with temperature is a change in the material properties with temperature of the dielectric materials that comprise the layers of the filters.

FIG. 1 shows a schematic of a typical structure of a narrow bandpass interference filter. The narrow bandpass interference filter 5 comprises layers of high (H) refractive index material 10 and low (L) refractive index material 12 deposited on a substrate (S) 12. A Fabry-Perot cavity 2L 16 is formed in a section of the narrow bandpass interference filter 5. Ray traces are shown for an angle of incidence θ 18 for an incident radiation beam (beam refraction at the various interfaces is omitted for purposes of clarity).

The narrow bandpass interference filter 5 comprises the Fabry-Perot cavity 16 formed from low refractive index material (shown as 2L) separating two stacks of alternating high and low refractive index materials (shown as HLHL-HLH). The layers are deposited onto the substrate 14, which may comprise silicon, germanium or sapphire. The cavity 16 behaves as a Fabry-Perot interferometer and the condition for the transmission of radiation of wavelength $\lambda_o$ through the filter is given by:

$$\frac{m\lambda_o}{2} = n_o d_o \cos\vartheta \qquad [1]$$

where:
$n_o$ is the refractive index of the cavity film,
$d_o$ is the thickness of the cavity film,
θ is the angle of incidence of the radiation and m is an integer, usually referred to as the order of the interference.

The term $n_o d_o \cos\theta$ is the optical thickness of the Fabry-Perot cavity 16, and for transmission through the narrow bandpass interference filter 5 the optical thickness must be equal to an integer number of half wavelengths, i.e., the condition for constructive interference between incident and reflected light at the boundary of the cavity. The layers bounding the Fabry-Perot cavity 16 are stacks of high reflectivity quarter wavelength layers characterised by:

$\lambda_o/4 = n_H d_H \cos\theta$ and $\lambda_o/4 = n_L d_L \cos\theta$ where the subscripts H and L refer to the high and low refractive index materials, respectively.

For narrow bandpass filters operating in the mid-infrared spectral region low refractive index materials may comprise zinc selenide and zinc sulfide, while the high refractive index materials may comprise germanium and lead telluride.

At some temperature T, for the same order m and angle of incidence θ, $$\frac{m\lambda_T}{2} = n_T d_T \cos\vartheta \qquad [2]$$

and combining eqns. [1] and [2] gives:

$$\lambda_T = \frac{(n_T d_T)}{(n_o d_o)}\lambda_o \qquad [3]$$

or $$\Delta\lambda = \lambda_T - \lambda_o = \lambda_o\left[\frac{(n_T d_T)}{(n_o d_o)} - 1\right] \qquad [4]$$

which identifies the source of the temperature shift in the centre wavelength of the filter as the change in the optical thickness of the cavity.

The changes in n and d with temperature result from a combination of thermal expansion (∂d/∂T), thermooptic (∂n/∂T), thermomechanical (∂d/∂σ) and stress optic (∂n/∂σ) effects, where σ is the stress developed in the layers of the film and the substrate caused by differential thermal expansion effects.

FIGS. 2A-D show the temperature dependence of the bandpass of four commercially-available mid-IR filters operating in the spectral region 3.0-5.3 µm. All four filters experience a systematic decrease in Tm and an increase in $\lambda_m$ as the temperature increases from 25 to 200° C.

Figure 3A:
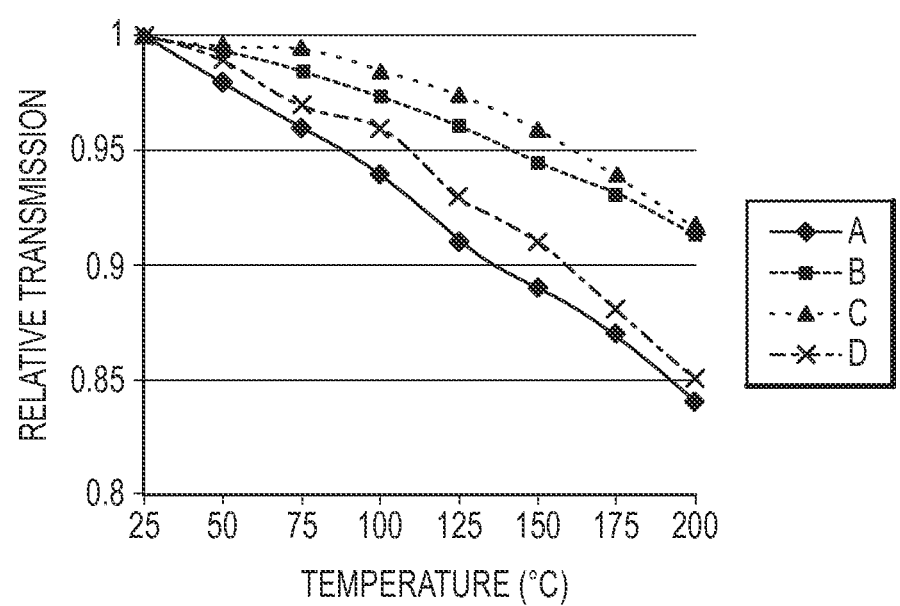
FIG. 3A shows the relative change in Tm for the four filters of FIGS. 2A-2D as a function of temperature.

FIG. 3A shows the relative change in Tm for the four filters as a function of temperature. Filters A and D experience a 15-16% decrease in Tm over the temperature range, while the decrease for filters B and C is only 8%. The value of dTm/dT increases with increasing temperature for filters B, C and D but is fairly constant over the whole temperature range for filter A.

Figure 3B:
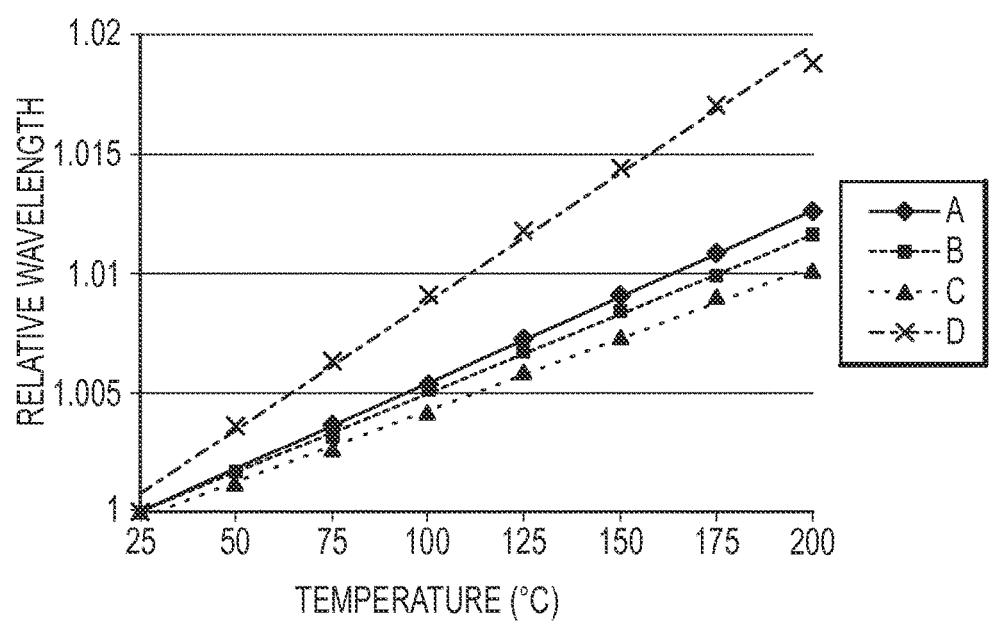
FIG. 3B shows the dependence of the relative wavelength ($\lambda_m(T)/\lambda_m(25)$) on temperature for the four commercially-available filters of FIGS. 2A-2D.

FIG. 3B shows the dependence of the relative wavelength ($\lambda_m(T)/\lambda_m(25)$) on temperature for the four commercially-available filters. The corresponding values of $d\lambda_m/dT$ for filters A, B, C and D are 0.21, 0.23, 0.25 and 0.57 nm/K, which are comparable to the values (or moduli of the values) of $d\lambda_m/dT$ obtained previously (4-6, 16-19) for mid-IR filters.

Optical mechanical models of increasing complexity have been used to account for the change in optical properties, such as the shift in the centre wavelength, of narrow bandpass filters with changes in temperature. In one such model, the shift in wavelength with temperature of the narrowband pass filter, $d\lambda_m/dT$, is simply considered as being related to the coefficient of thermal expansion ($C_s$) of the substrate and $dn_e/n_e dT$, where $n_e$ is the effective refractive index of the filter layers.

Figure 4:
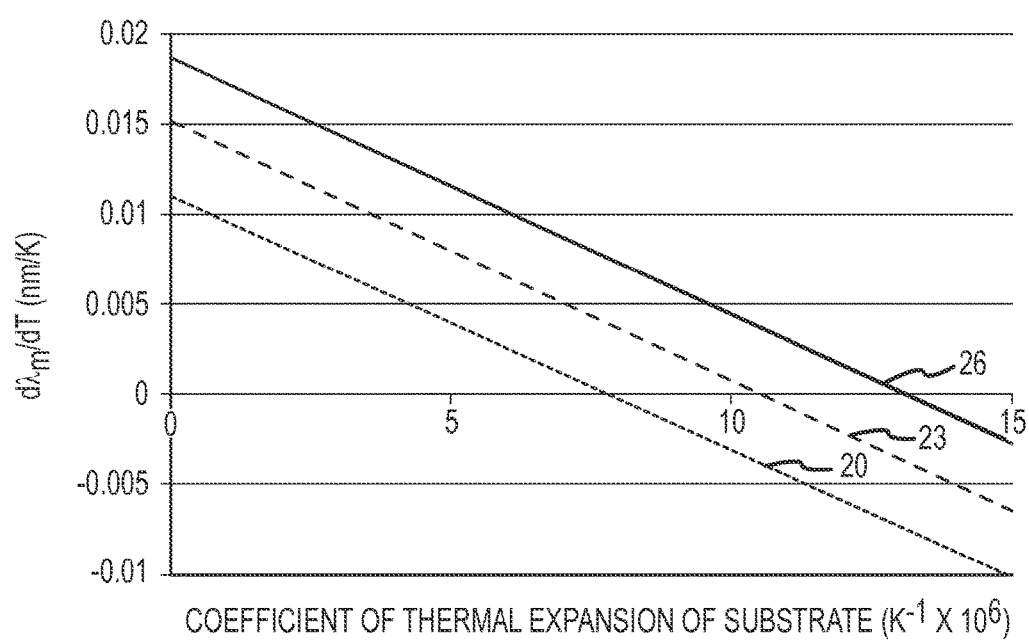
FIG. 4 illustrates dependence of $d\lambda_m/dT$ on coefficients of thermal expansion of substrate ($C_s$) for three values of $dn_e/n_e dT$; 0.75×10-5 K−1 (bottom), 1.00×10-5 K-I (middle), and 1.25×10-5 K-I (top)

FIG. 4 shows the dependence of the shift in wavelength at peak transmission with temperature ($d\lambda_m/dT$) as a function of the coefficient of thermal expansion ($C_s$) for three values of refractive index change of the materials comprising the filter with temperature ($dn_e/n_e dT$), as obtained by one such optical mechanical model. In FIG. 4, $dn_e/n_e dT$ is $0.75 \times 10^{-5}$ K$^{-1}$ 20, $1.00 \times 10^{-5}$ K$^{-1}$ 23 and $1.25 \times 10^{-5}$ K$^{-1}$ 26.

The figure shows that $d\lambda_m/dT$ can be related to $dn_e/n_e dT$ and $C_s$ by:

$$\frac{d\lambda_m}{dT} = k_1 \frac{dn_e}{n_3 dT} + k_2 C_s + k_3 \quad [5]$$

where $k_1$, $k_2$ and $k_3$ are constants. For the data shown in FIG. 4:

$$\frac{d\lambda_m}{dT} = 1540 \frac{dn_e}{n_3 dT} - 1400 C_s - 0.004 \quad [6]$$

which shows that the coefficients for the relative changes in the effective refractive index and dimensional changes of the substrate are approximately equal.

In the near-IR spectral region the modulus of the relative change in the refractive index of the dielectrics typically used to fabricate filters ($SiO_2$, $TiO_2$, $Al_2O_3$ and $Ta_2O_5$) is in the range $1-10 \times 10^{-6}$ $K^{-1}$ and therefore comparable to the values of $C_s$ for some glass substrates. Under these circumstances it is possible to minimise the value of $d\lambda_m/dT$ by balancing the changes in $n_e$ with the changes in the physical dimensions of the dielectric films and substrate.

The dielectric materials used to fabricate filters in the mid-IR spectral region are characterised by significantly larger values of dn/ndT than those materials used in the near-IR. Common high and low refractive index materials used to construct mid-IR filters are germanium (Ge) and zinc selenide (ZnSe), which have values of dn/ndT of $10.8 \times 10^{-5}$ $K^{-1}$ and $2.5 \times 10^{-5}$ $K^{-1}$, respectively. Application of the optical mechanical model by means of equation 6 with $C_s$ set to zero gives $d\lambda_m/dT=0.04$ nm/K for zinc selenide and $d\lambda_m/dT=0.17$ nm/K for germanium, Note these are values determined from a simple model and when the values of dn/ndT for the mid-IR optical materials zinc selenide and germanium are used in equation 6, the values of $d\lambda/dT$ obtained from the model are of the order of 0.2-0.8 nm/K, the values of $d\lambda_m/dT$ measured experimentally for mid-IR filters. Such a large shift in wavelength at peak transmission with temperature ($d\lambda_m/dT$) for mid-IR filters limits the use of such filters in industries where the filter is to be used in temperature varying conditions.

In an embodiment of the present disclosure, a mid-infrared narrow bandpass filter is provided that has substantially temperature invariant optical properties over a wide temperature range. The temperature range is $-20°$ C. to $+200°$ C. and the measured modulus of the shift in the wavelength $\lambda_m$ at maximum transmission with temperature, $d\lambda_m/dT$, is less than 0.2 nm/K over the wavelength range 2-14 μm.

An approach to the design of filters with a predetermined thermal response can be considered by the design of the filter:

$$(LH)^{x_1}(LL)^{y_1}(HL)^{x_2}(LL)^{y_2} \ldots (LL)^{y_N}(HL)^{x_{N+1}}$$

consisting of a total of y half wavelength spacers (cavities) LL of low refractive index material in N cycles ($y=\Sigma y_i$) and where LH are the stacks of $x_i$ quarter wavelength layers of alternating high and low refractive index material in the N cycles.

The peak reflection wavelength of the quarter wavelength reflector stack, irrespective of the values of $x_i$ and N, can be expressed as $$\lambda_m = 2(n_L d_L + n_H d_H) \quad [7]$$

for first order reflections (m=0).

The temperature variation of the wavelength in the reflector stack $d\lambda_m/dT|_s$ can be expressed as $$\left.\frac{d\lambda_m}{dT}\right|_s = 2n_L d_L \left(C_L + \frac{dn_L}{n_L dT}\right) + 2n_H d_H \left(C_H + \frac{dn_H}{n_H dT}\right) \quad [8]$$

where $C_L$ and $C_H$ are the coefficients of linear expansion of the low and high refractive index materials, respectively.

From eqn. [1] for first order reflection and normal incidence (i.e., m=1 and θ=0°), the corresponding temperature dependence $d\lambda_m/dT|_c$ of the cavity layer of low refractive index material is given by:

$$\left.\frac{d\lambda_m}{dT}\right|_c = 2yn_L d_L \left(C_L + \frac{dn_L}{n_L dT}\right) \quad [9]$$

noting that y is the total number of half wavelength cavity layers.

The total change in wavelength with temperature $d\lambda_m/dT|_T$ is given by the sum of $d\lambda_m/dT|_c$ and $d\lambda_m/dT|_s$ $$\left.\frac{d\lambda_m}{dT}\right|_T = 2(1+y)n_L d_L \left(C_L + \frac{dn_L}{n_L dT}\right) + 2n_H d_H \left(C_H + \frac{dn_H}{n_H dT}\right) \quad [10]$$

or $$\left.\frac{d\lambda_m}{\lambda_m dT}\right|_T = (1+y)\left(C_L + \frac{dn_L}{n_L dT}\right) + \left(C_H + \frac{dn_H}{n_H dT}\right) \quad [11]$$

noting $n_L d_L = n_H d_H$ at the temperature for which the filter is designed for use.

From the preceding, it can be seen that $d\lambda_m/dT|_T$ can only be zero if the value of dn/dT for one of the materials is negative. As such, in embodiments of the present disclosure, a high refractive index material, such as PbTe, is used in the filter to provide a negative value of dn/dT. In embodiments of the present disclosure, for close matching of the value of $d\lambda_m/dT|_T$ to zero, the wavelength dependence of $n_i$ with temperature and wavelength dependence of $dn_i/dT$ is taken into account.

The condition $d\lambda_m/dT|_T=0$ is given approximately by:

$$\frac{dn_H}{n_H dT} = -(1+y)\frac{dn_L}{n_L dT} \quad [12]$$

noting that $C_i$ is considerably smaller than $dn_i/n_i dT$ for most materials used in mid-infrared filters. In embodiments of the present disclosure, the term (1+y) may be chosen to satisfy eqn. [12] depending on the choice of low refractive index material. For example, in one embodiment of the present disclosure, with ZnSe for the low refractive index material and PbTe for the high refractive index material of the lens, and using the material values of bulk phases $n_L=2.43$, $n_H=6.10$, $dn_L/dT=6.3 \times 10^{-5}$ $K^{-1}$ and $dn_H/dT=-2.1 \times 10^{-3}$ $K^{-1}$ for $\lambda_m=3.4$ μm, eqn. [12] is satisfied with y=13.3, i.e., approximately 13 half wavelength cavity layers are required to achieve the condition $d\lambda_m/dT|_T=0$.

There is considerable variation in the values of the material properties ($n_H$, $dn_H/dT$, $C_H$, etc.) that appear in eqn. [11] for thin films in a multilayer structure and therefore in the predicted value of $d\lambda_m/\lambda_m dT$ or the value of y required to achieve the condition $d\lambda_m/\lambda_m dT=0$. The uncertainty is particularly severe for the value of $dn_H/dT$ for PbTe in view of its magnitude and influence on the value of y. For example, the value of dn/dT for PbTe at $\lambda_m=5$ μm has been reported to be of the order of $-1.5\times10^{-3}$ $K^{-1}$, $-2.7\times10^{-3}$ $K^{-1}$ and $-2.8\times10^{-3}$ $K^{-1}$. From eqn. [12] the corresponding values of y (to the nearest integer) are 9, 17 and 18, respectively.

In view of the uncertainties in the value of dn/dT for PbTe and, therefore, the number of low refractive index half wavelength spacers required to achieve $d\lambda_m/dT=0$, in embodiments of the present disclosure, applicants have determined an experimental value of $d\lambda_m/dT$ as a function of the optical thickness of the low refractive index cavities for a suite of filters. In determining the experimental value the suite of filters are fabricated by the same method. From the experimental analysis it is possible, unlike with the lens models, to make a determination for a configuration of a narrow bandpass filter that has a minimal or zero value for $d\lambda_m/dT$ under specified conditions, such as a specified temperature variation.

Figure 5:
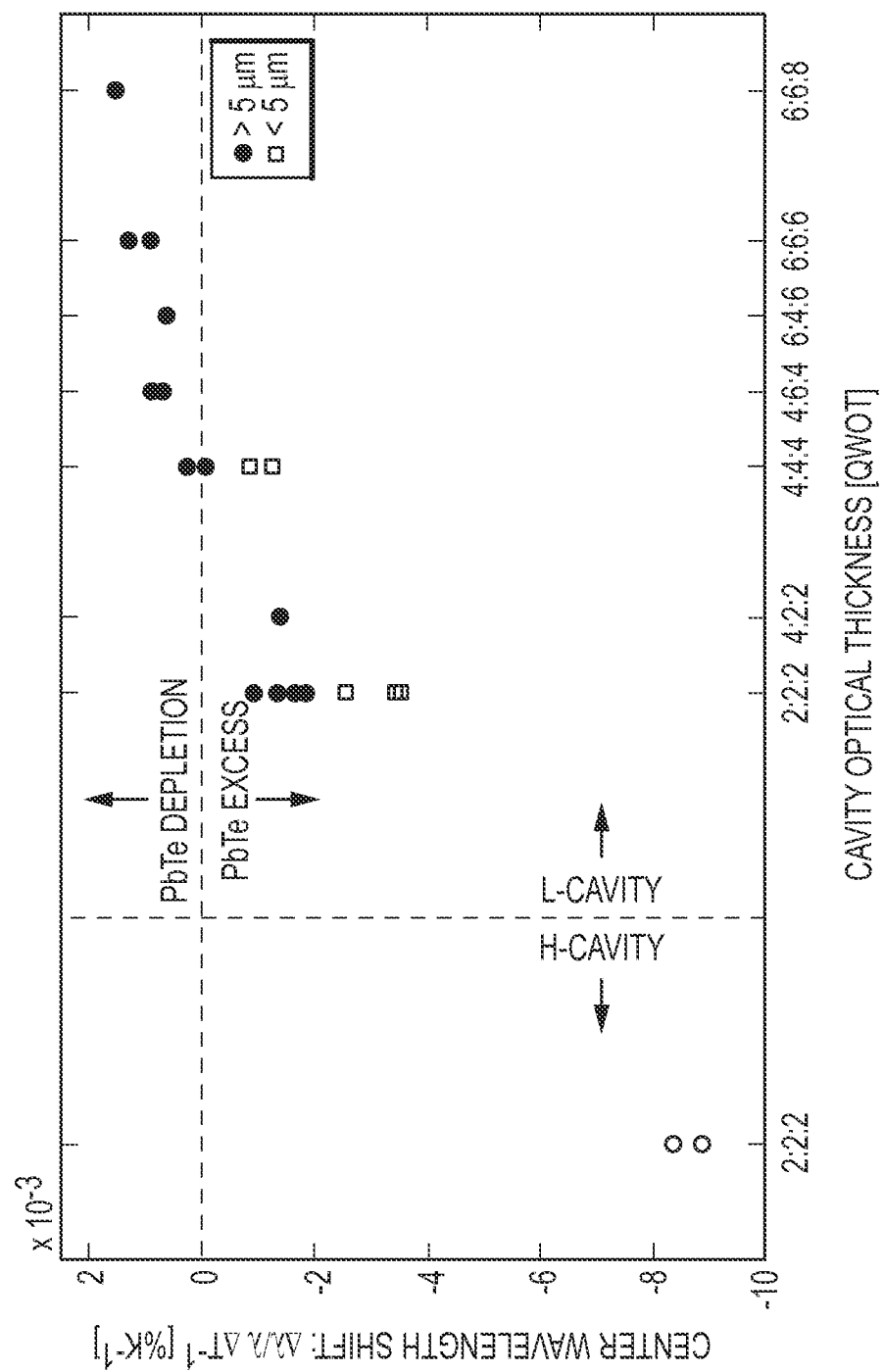
FIG. 5 illustrates variation of $d\lambda_m/\lambda_m dT$ for a suite of filters, in accordance with embodiments of the present disclosure, fabricated with ZnSe as the low refractive index material and PbTe as the high refractive index material.

FIG. 5 shows the variation of $d\lambda_m/\lambda_m dT$ for a suite of filters, in accordance with embodiments of the present disclosure, fabricated with ZnSe as the low refractive index material and PbTe as the high refractive index material. The plot shows that, in accordance with embodiments of the present disclosure, a particular value of $d\lambda_m/\lambda_m dT$ can be achieved by controlling the ratio of low to high refractive index materials in the filter (i.e., a parameter similar to y in eqns. [11] and [12]). From analysis, it was found that to obtain temperature invariance, the ration of low refractive index to high refractive index material needs to be high. As such, in embodiments of the present disclosure, the narrow bandpass filter comprises one or more cavities comprising low refractive index material. FIG. 5 shows that for $\lambda_m<5$ μm the condition $d\lambda_m/\lambda_m dT=0$ is met by a 4:4:4 (i.e., 3 full wavelength or 6 half wavelength cavities (y=6)) filter, while for $\lambda_m>5$ μm a 6:4:6 (y=8) filter is required. As such, in some embodiments of the present invention, to a ratio/amount of low refractive index to provide temperature invariance the filter comprises one or more cavities that provide an optical thickness of at least three full wavelengths of the transmission wavelength.

In accordance with an embodiment of the present disclosure, a narrow bandpass filter is provided that comprises cavities having a low refractive index. In accordance with embodiments of the present disclosure, the design procedure illustrated in FIG. 5 may be used to fabricate substantially temperature invariant filters over the entire mid-infrared spectral range. To provide for temperature invariance, the narrow bandpass filter includes a large amount of low refractive index material, film and/or the like. Consequently, in accordance with some embodiments of the present disclosure, the temperature invariant narrow bandpass filter comprises a cavity(ies) having an optical thickness of at least three full wavelengths of the transmission wavelength or the narrow band of transmission wavelengths or three half-wavelengths of the transmission wavelength or the narrow band of transmission wavelength.

The cavity may comprise a single or a plurality of cavities that provide the optical thickness. Merely by way of example where the filter comprises three cavities of low refractive index material, each of the cavities comprises either half wavelength ($\lambda/2$) or full wavelength ($\lambda$) of the transmitted radiation in thickness. Where the filter comprises a single cavity, the cavity comprises an optical thickness of at least $3\lambda/2$ or $3\lambda$ in thickness. Other combinations, such as a two cavity, one $\lambda/2$ cavity and one $\lambda$ cavity, are also possible to provide the desired optical thickness.

In some embodiments, the temperature invariant filter comprises a cavity or a plurality of cavities, where the optical thickness of the cavity or the cavities comprises at least three full wavelengths of the transmission wavelength or six half-wavelengths of the transmission wavelength, i.e, an equivalent y value of 6 or greater. Such a configuration, although complicated to fabricate, provides a large ratio of low refractive index material to produce temperature invariance.

Moreover, as described herein, new materials have been used as low and/or high refractive index materials in the narrow bandpass filter to provide, amongst other things, for spectral transmission through the narrow bandpass filter, as the prior materials for fabricating narrow bandpass filters do not work or perform poorly with the configuration of the temperature invariant narrow bandpass filters of the present disclosure.

FIGS. 6A and B illustrate a system comprising a modified thin film deposition system with rotating thermal evaporation sources and stationary optical substrates for fabricating a temperature invariant filter in accordance with an embodiment of the present disclosure. FIG. 6A is an illustration of a Balzers BA510 thin film deposition system and FIG. 6B is a schematic of the rotating evaporation sources.

In an embodiment of the present disclosure, coating depositions may be fabricated using a specially modified Balzers 510 bell-jar deposition plant containing a unique geometry of rotating thermal evaporation sources and stationary substrates. In embodiments of the present disclosure, the deposition layer materials are evaporated from resistance heated molybdenum boat sources mounted on a slip ring assembly rotating at a fixed geometry beneath the substrate plane. This static-substrate arrangement permits precise temperature control of the substrates, aided by jig mounting with intimate thermo-mechanical contact during deposition. The static substrate plant arrangement allows precise control of substrate temperature using intimate coating jig attachment to an electrically heated copper backing plate which ensures the uniformity, stoichiometry and packing density of the deposited condensed films.

In an embodiment of the present disclosure, control of the substrate temperature is achieved by intimate contact clamping using a combination of metallic lead annular washers, backing pieces and slotted disc springs. This arrangement provides a low impedance thermal path from the uncoated substrate rim to the temperature controlled coating jig maintaining a constant substrate temperature despite the variable radiated flux that originates from the evaporation sources. Temperature control is critically important as the 'sticking coefficient' of most infrared materials is strongly dependent on temperature. Reproducibility of this method also ensures that there is a minimum of variation between the filter substrate and optical monitor piece used to determine layer thickness during the deposition.

Narrow bandpass filters, in accordance with embodiments of the present disclosure, were fabricated using ZnS and ZnSe substrates with PbTe as the high refractive index material and ZnSe as the low refractive index material in the reflecting stacks and ZnSe as the low refractive index material in the cavity layers. The filters were designed with 19 layers of quarter wavelength thickness of ZnSe and PbTe with three cavity layers consisting of either half or full wavelength thickness. The multilayer bandpass design and choice of substrate material were selected for perfect optical impedance matching. However, in some embodiments, additional substrates of differing material were included in the filters to produce optical matching. These filters, in accordance with embodiments of the present disclosure, are referred to as 'degenerate' and are of considerable use for optical and environmental diagnosis purposes, particularly the identification of any dependencies on the choice of substrate.

Figure 7A:
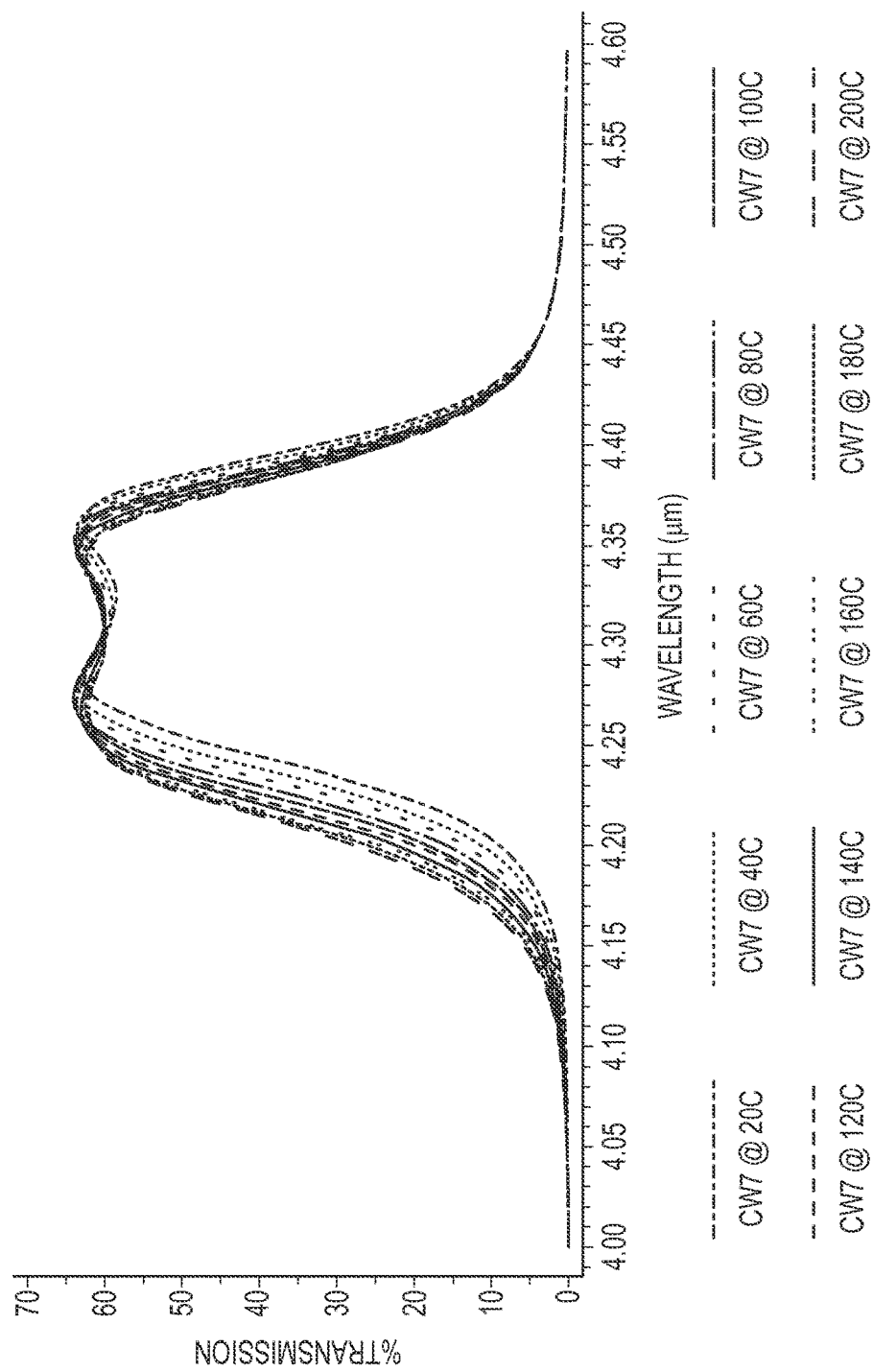
FIGS. 7A and 7B show the temperature dependence of the bandpass of two 3 cavity filters fabricated on ZnSe substrates and designed to operate at $\lambda_m$=4.26 μm, in accordance with embodiments of the present disclosure.
Figure 7B:
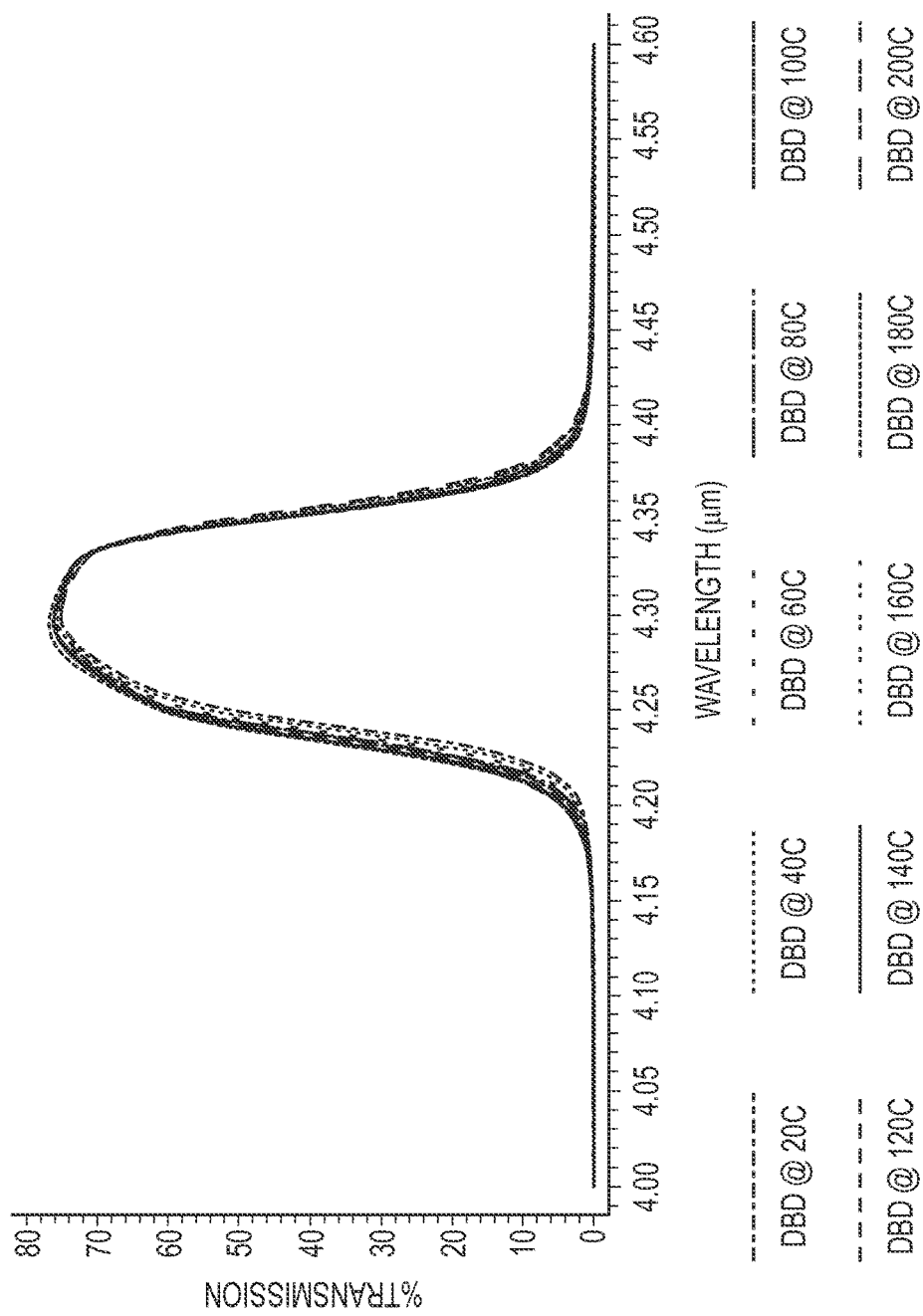

FIGS. 7A and 7B show the temperature dependence of the bandpass of two 3 cavity filters fabricated on ZnSe substrates and designed to operate at $\lambda_m$=4.26 μm, in accordance with embodiments of the present disclosure.

FIG. 7A shows the performance of a degenerate filter consisting of 3 half wavelength cavities (2:2:2). Performance of the filter shows a systematic shift of $\lambda_m$ to shorter wavelength with increasing temperatures (i.e., $d\lambda_m/\lambda_m dT<0$).

In contrast, in accordance with an embodiment of the present disclosure, FIG. 7B shows the performance of a filter with optimum optical matching and 3 full wavelength thickness cavities (4:4:4). Performance of the filter shows a significantly smaller shift with temperature.

Figure 8B:
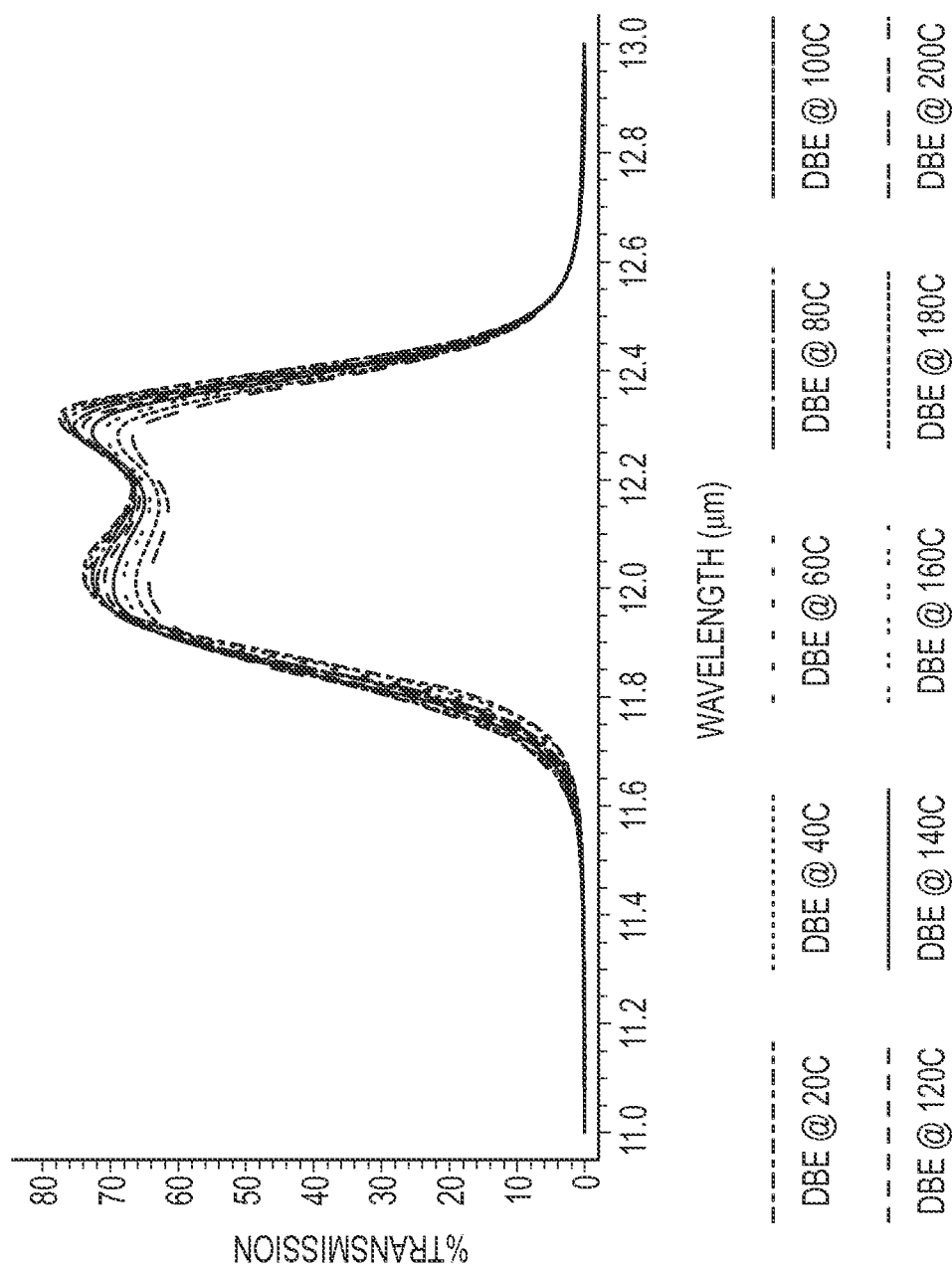

FIGS. 8A and 8B show the corresponding performance of two narrow bandpass filters, a degenerate filter in FIG. 8A and an optimally matched filter in FIG. 8B, operating at $\lambda_m$=12.12 μm. As shown in Fills. 8A and 8B, the two filters, both constructed with 3 half wavelength cavities (2:2:2), show similar behavior, both in terms of wavelength shift and decrease in transmission with increasing temperature.

Figure 9:
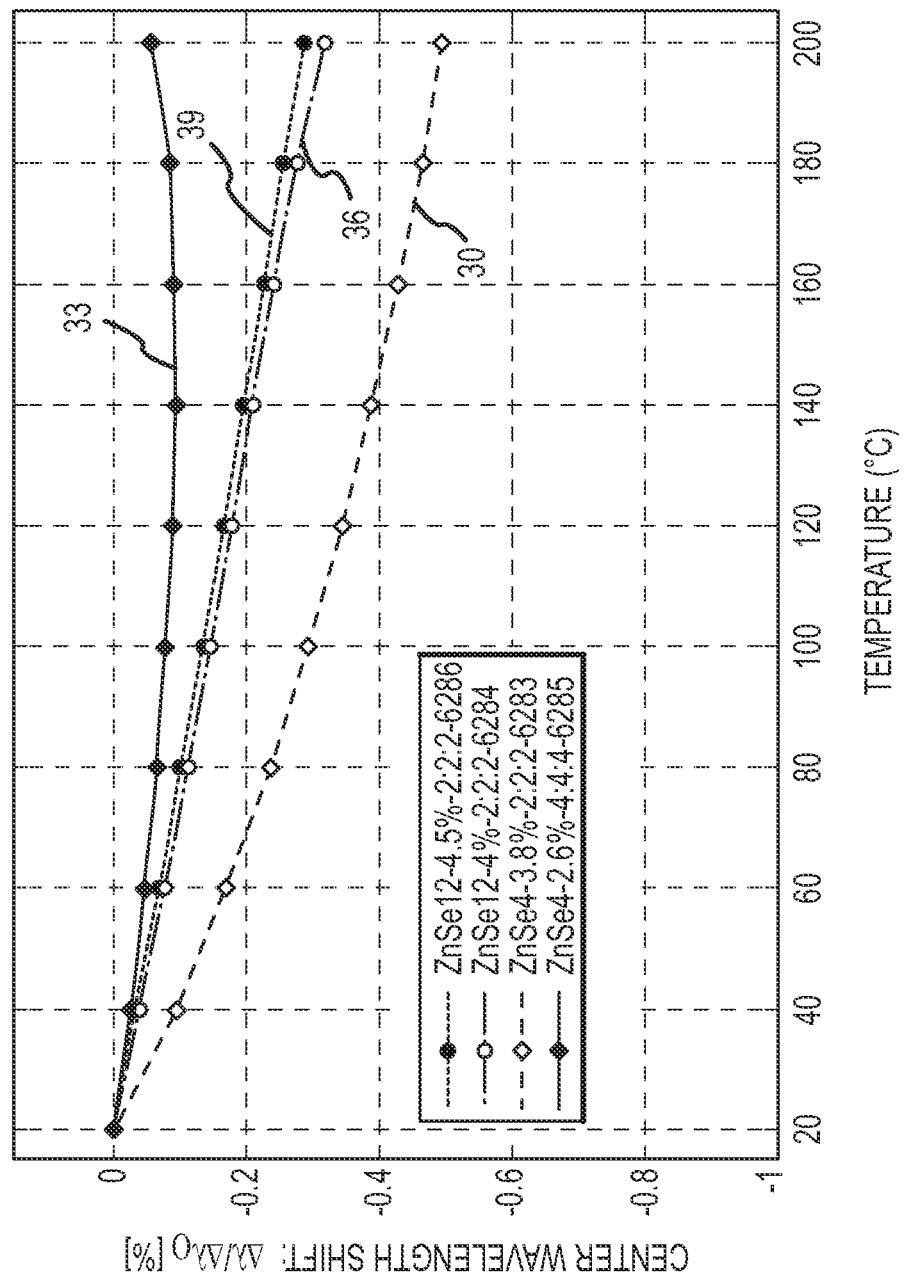
FIG. 9 compares the relative change in wavelength $\lambda_m$ at peak transmission with temperature of the four filters shown in FIGS. 7A and 7B and 8A and 8B.

FIG. 9 compares the relative change in wavelength $\lambda_m$ at peak transmission with temperature of the four filters having their performance shown in FIGS. 7A, 7B, 8A, and 8B: degenerate 4.26 μm (2:2:2) (line 30), optimally matched 4.26 μm (4:4:4) (line 33), degenerate 12.1 μm (2:2:2) (line 36), and optimally matched 12.1 μm (2:2:2) (line 39), respectively. In FIG. 9, therefore, the degenerate 4.26 μm (2:2:2) filter produces line 30, the optimally matched 4.26 μm (4:4:4) filter produces line 33, the degenerate 12.1 μm (2:2:2) filter produces line 36, and the optimally matched 12.1 μm (2:2:2) filter produces line 39.

The change in $\lambda_m$ is expressed as $\Delta\lambda_m/\lambda_{mo}$, where $\lambda_{mo}$ is the value of $\lambda_m$ at 20° C. The value of $d\lambda_m/dT$ for the $\lambda_m$=4.26 μm (4:4:4) filter varies from −0.04 nm/K at 20° C. to +0.03 nm/K at 200° C. and sensibly zero over the temperature range 80-160° C. The maximum numerical value of $d\lambda_m/dT$ for the $\lambda_m$=4.26 μm (2:2:2) filter is −0.21 nm/K at 20° C. with an average value of −0.12 nm/K over the whole temperature range. The values of $d\lambda_m/dT$ for the $\lambda_m$=12.1 μm (2:2:2) optimal and degenerate filters are −0.19 and −0.21 nm/K, respectively, over the temperature range 20-200° C.

Figure 10:
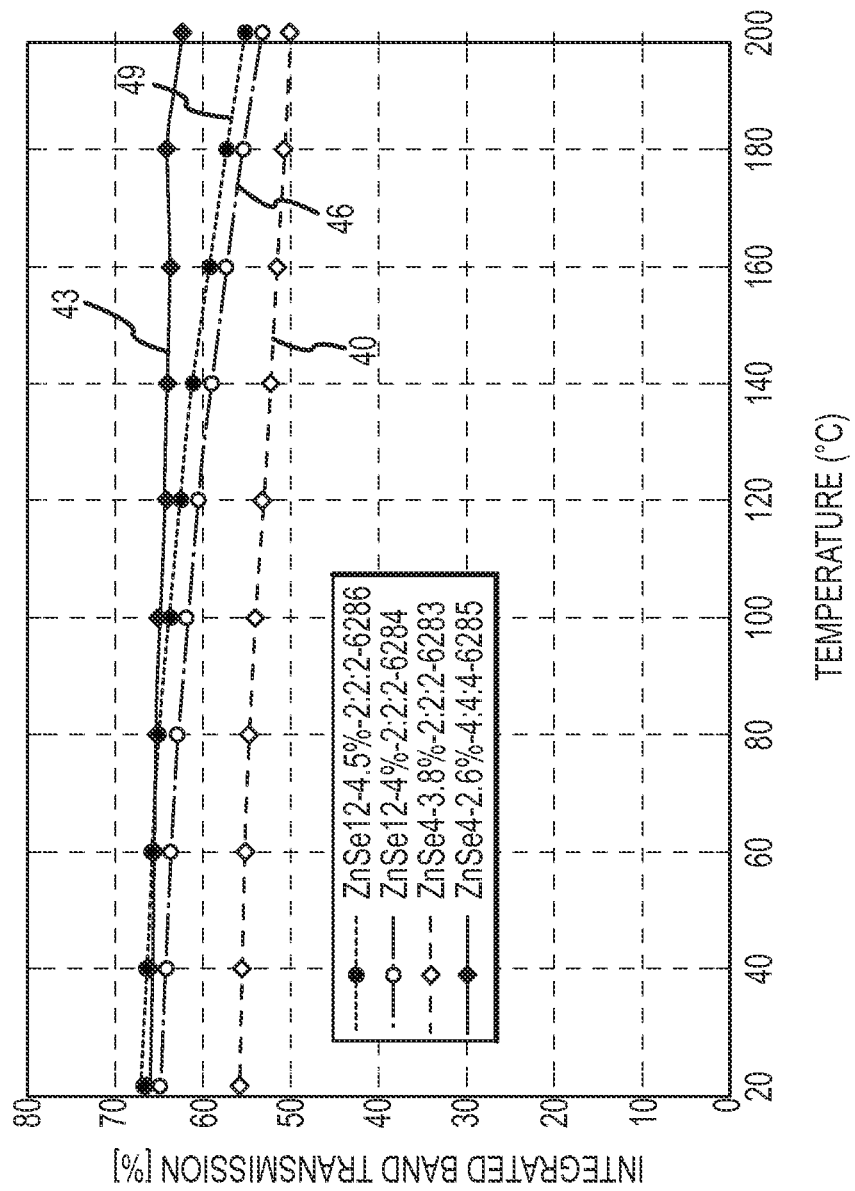
FIG. 10 shows the corresponding variation of the integrated band transmission Ti with temperature for the four filters of FIGS. 7A and 7B and 8A and 8B.

FIG. 10 shows the corresponding variation of the integrated band transmission Ti with temperature for the four filters having their performance shown in FIGS. 7A, 7B, 8A, and 8B: degenerate 4.26 μm (2:2:2) (line 40), optimally matched 4.26 μm (4:4:4) (line 43), degenerate 12.1 μm (2:2:2) (line 46), and optimally matched 12.1 μm (2:2:2) (line 49), respectively. In FIG. 10, the value of dTi/dT is negligible for the $\lambda_m$=4.26 μm (4:4:4) filter, and |dTi/dT| is less than 0.06%/K for the other 3 filters. In the figure, the degenerate 4.26 μm (2:2:2) filter produces line 40, the optimally matched 4.26 μm (4:4:4) filter produces line 43, the degenerate 12.1 μm (2:2:2) filter produces line 46, and the optimally matched 12.1 μm (2:2:2) filter produces line 49.

Figure 11B:
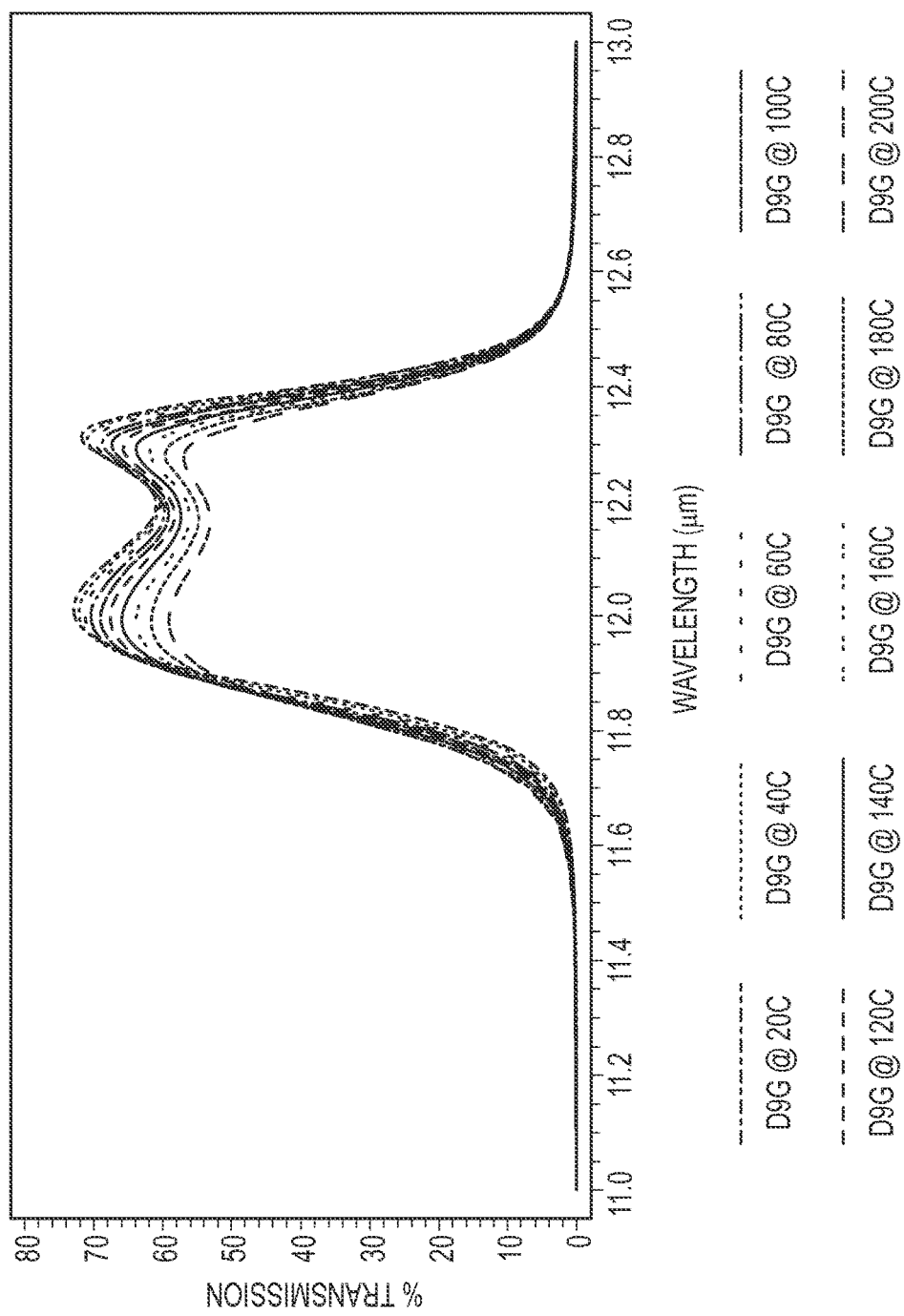

FIGS. 11A and B show the temperature dependence of the bandpass of two 3 cavity filters fabricated on ZnS substrates that have been designed to operate at $\lambda_m$=4.26 μm (4:4:4 cavity layers) and $\lambda_m$=12.1 μm (2:2:2 cavity layers). Both filters have been optically matched to the substrate (i.e., are non-degenerate).

Figure 12:
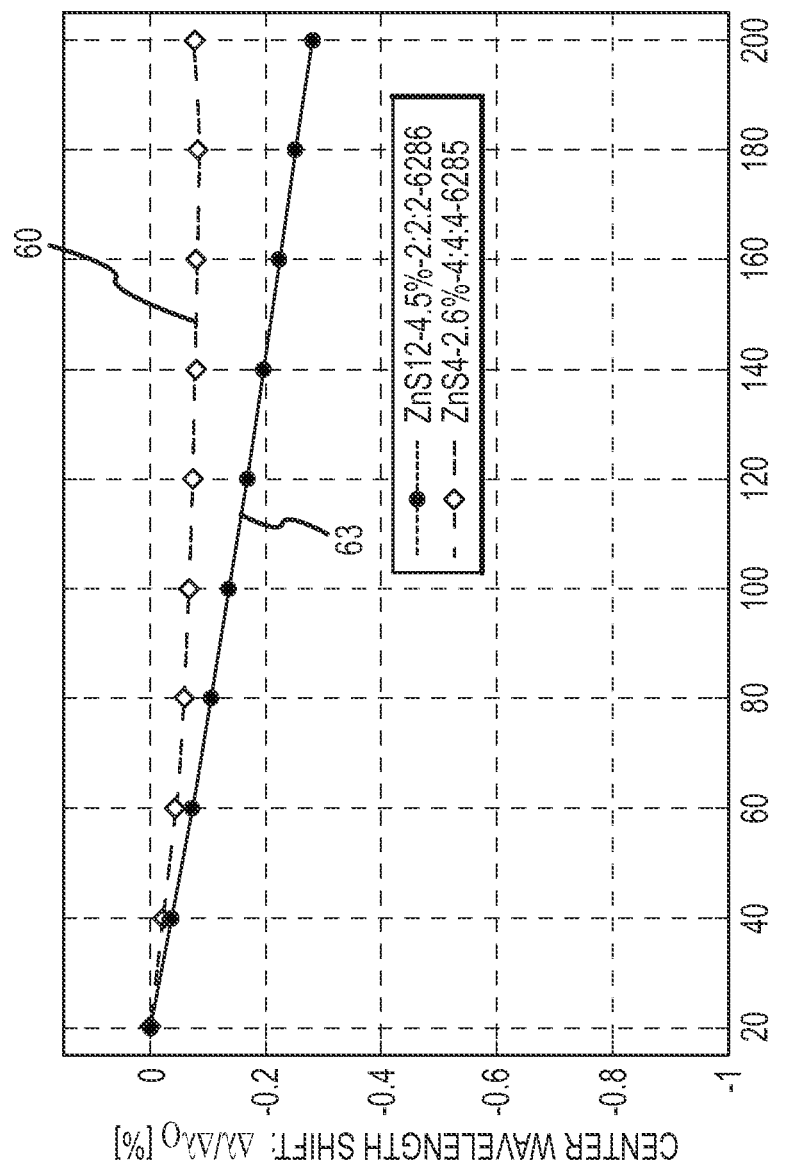
FIG. 12 compares the dependence of $\lambda_m/\lambda_{mo}$ on temperature (20-200° C.) for the two filters shown in FIGS. 11A and 11B.

FIG. 12 compares the dependence of $\Delta\lambda_m/\lambda_{mo}$ on temperature (20-200° C.) for the two filters shown in FIG. 11. In the figure, variation of $\Delta\lambda_m/\lambda_{mo}$ with temperature for the 4.26 μm (4:4:4) filter 60 and the 12.1 μm (2:2:2) 63 are shown.

The largest absolute value of $d\lambda_m/dT$ for the $\lambda_m$=4.26 μm filter is −0.05 nm/K, which is obtained at 20° C.; $d\lambda_m/dT$ is sensibly zero over the temperature range 80-200° C. The $\lambda_m$=12.1 μm filter exhibits a value of $d\lambda_m/dT$=−0.19 nm/K over the entire temperature range.

FIG. 13 shows the variation of Ti with temperature for the two filters deposited on ZnS substrates. In the figure, variation of integrated band transmission with temperature for the 4.26 μm (4:4:4) filter 66 and the 12.1 μm (2:2:2) 69 are shown. The decrease in Ti for the $\lambda_m$=12.1 μm filter is 15% over the temperature range 20-200° C., while the corresponding decrease for the $\lambda_m$=4.26 μm filter is less than 5%.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions and alterations herein without departing from such scope.

All references referred to above are hereby incorporated by reference.

The invention claimed is:

1. A temperature invariant narrow bandpass filter configured to transmit mid-infrared radiation with a transmission wavelength or narrow band of transmission wavelengths, the temperature invariant narrow bandpass filter comprising:
   a substrate;
   a first stack comprising layers of alternating high and low refractive index materials deposited on the substrate;
   a cavity comprising low refractive index material deposited on the first stack; and
   a second stack comprising layers of alternating high and low refractive index materials deposited on the cavity, wherein:
      the high refractive index materials have a refractive index that decreases with temperature over a portion of an operating temperature of the temperature invariant narrow bandpass filter;
      the cavity is disposed between the first and the second stack; and
      the cavity comprises an optical thickness of at least three full wavelengths of the transmission wavelength or the narrow band of transmission wavelengths or three half-wavelengths of the transmission wavelength or the narrow band of transmission wavelengths;
   wherein a modulus of change in central wavelength of the temperature invariant narrow bandpass filter with temperature is less than or equal to 0.2 nm/° C. over a temperature range of about −25° C. to about +200° C. for a wavelength range of about 2 to 14 micrometers.

2. The temperature invariant narrow bandpass filter of claim 1, wherein the cavity comprises three separate cavities and each of the three separate cavities comprises an optical thickness of either a full wavelength (λ) of the transmission wavelength or the narrow band of transmission wavelengths or a half wavelength (λ/2) of the transmission wavelength or the narrow band of transmission wavelengths.

3. The temperature invariant narrow bandpass filter of claim 1, wherein the cavity comprises a plurality of separate cavities that in combination comprise an optical thickness of at least three full wavelengths of the transmission wavelength or the narrow band of transmission wavelengths or three half-wavelengths of the transmission wavelength or the narrow band of transmission wavelengths.

4. The temperature invariant narrow bandpass filter of claim 1, further comprising:
one or more additional stacks of alternating high and low refractive index material.

5. The temperature invariant narrow bandpass filter of claim 1, wherein the low refractive index material comprises at least one of zinc selenide and zinc sulfide.

6. The temperature invariant narrow bandpass filter of claim 1, wherein the high refractive index material comprises lead sulfide, lead selenide, lead telluride, or a combination of lead telluride, lead sulfide and lead selenide.

7. The temperature invariant narrow bandpass filter of claim 1, wherein a relationship between the number of half wavelength and full wavelength cavities and the change in central wavelength of the temperature invariant narrow bandpass filter with temperature is established to obtain a particular value of the change in central wavelength with temperature, including a value that is sensibly zero, by the fabrication of a suite of temperature invariant narrow bandpass filters with a varying number of the cavities using a particular fabrication method and with particular materials for the high and low refractive index layers.

8. The temperature invariant narrow bandpass filter of claim 1, wherein the low refractive index material comprising the cavity is different from the low refractive index material of at least one of the first stack and the second stack.

9. The temperature invariant narrow bandpass filter of claim 1, wherein the cavity has a number of half wavelength cavity layers that is 6 or greater.

10. The temperature invariant narrow bandpass filter of claim 1, wherein the cavity comprises an optical thickness of at least three full wavelengths of the transmission wavelength.

11. A temperature invariant narrow bandpass filter configured to transmit mid-infrared radiation with a transmission wavelength or narrow band of transmission wavelengths, the temperature invariant narrow bandpass filter comprising:
a substrate;
a first stack comprising layers of alternating high and low refractive index materials deposited on the substrate;
a cavity comprising low refractive index material deposited on the first stack; and
a second stack comprising layers of alternating high and low refractive index materials deposited on the cavity, wherein:
the high refractive index materials have a refractive index that decreases with temperature over a portion of an operating temperature of the temperature invariant narrow bandpass filter;
the cavity is disposed between the first and the second stack; and
the cavity comprises an optical thickness of at least three full wavelengths of the transmission wavelength or the narrow band of transmission wavelengths or three half-wavelengths of the transmission wavelength or the narrow band of transmission wavelengths;
wherein a modulus of change in peak transmission of the filter is less than about 0.1%/° C. over a temperature range of about −25° C. to about +200° C. for a wavelength range of about 2 to 14 micrometers.

12. The temperature invariant narrow bandpass filter of claim 11, wherein the cavity comprises three separate cavities and each of the three separate cavities comprises an optical thickness of either a full wavelength (λ) of the transmission wavelength or the narrow band of transmission wavelengths or a half wavelength (λ/2) of the transmission wavelength or the narrow band of transmission wavelengths.

13. The temperature invariant narrow bandpass filter of claim 11, wherein the cavity comprises a plurality of separate cavities that in combination comprise an optical thickness of at least three full wavelengths of the transmission wavelength or the narrow band of transmission wavelengths or three half-wavelengths of the transmission wavelength or the narrow band of transmission wavelengths.

14. The temperature invariant narrow bandpass filter of claim 11, further comprising:
one or more additional stacks of alternating high and low refractive index material.

15. The temperature invariant narrow bandpass filter of claim 11, wherein the low refractive index material comprises at least one of zinc selenide and zinc sulfide.

16. The temperature invariant narrow bandpass filter of claim 11, wherein the high refractive index material comprises lead sulfide, lead selenide, lead telluride, or a combination of lead telluride, lead sulfide and lead selenide.

17. The temperature invariant narrow bandpass filter of claim 11, wherein a relationship between the number of half wavelength and full wavelength cavities and the change in central wavelength of the temperature invariant narrow bandpass filter with temperature is established to obtain a particular value of the change in central wavelength with temperature, including a value that is sensibly zero, by the fabrication of a suite of temperature invariant narrow bandpass filters with a varying number of the cavities using a particular fabrication method and with particular materials for the high and low refractive index layers.

18. The temperature invariant narrow bandpass filter of claim 11, wherein the low refractive index material comprising the cavity is different from the low refractive index material of at least one of the first stack and the second stack.

19. The temperature invariant narrow bandpass filter of claim 11, wherein the cavity has a number of half wavelength cavity layers that is 6 or greater.

20. The temperature invariant narrow bandpass filter of claim 11, wherein the cavity comprises an optical thickness of at least three full wavelengths of the transmission wavelength.

* * * * *